Figure 1:
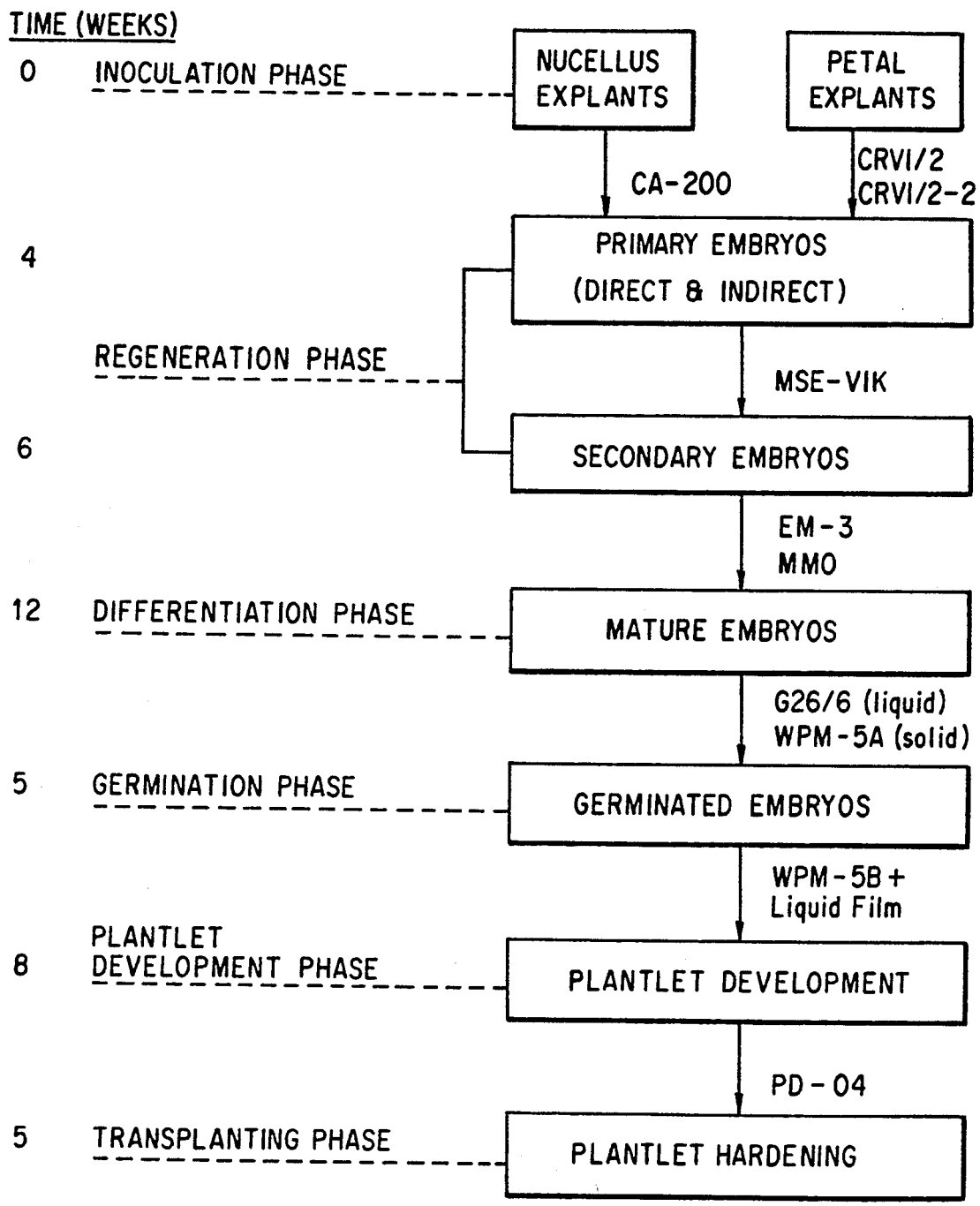

United States Patent [19]

Sondahl et al.

[11] Patent Number: 5,312,801
[45] Date of Patent: May 17, 1994

[54] SOMATIC EMBRYOGENESIS AND PLANT REGENERATION OF CACAO

[75] Inventors: Maro R. Sondahl, Mt. Laurel, N.J.; Zhenghua Chen, Beijing, China; Thomas B. Sereduk, Mt. Holly, N.J.; Claudia M. Bellato, Maple Shade, N.J.; Si-Jiu Liu, Delran, N.J.; Alvina Bragin, Cherry Hill, N.J.

[73] Assignees: DNA Plant Technology Corporation, Cinnaminson, N.J.; Hershey Foods Corporation, Hershey, Pa.

[21] Appl. No.: 814,853

[22] Filed: Dec. 30, 1991

Related U.S. Application Data

[63] Continuation-in-part of Ser. No. 419,296, Oct. 10, 1989, abandoned, which is a continuation-in-part of Ser. No. 43,864, Apr. 29, 1987, abandoned.

[51] Int. Cl.$^5$ ................................................ A01H 4/00
[52] U.S. Cl. .......................... 435/240.49; 435/240.45
[58] Field of Search ........... 435/240.4, 240.45, 240.48, 435/240.49, 240.51, 240.54; 800/200, 240

[56] References Cited

U.S. PATENT DOCUMENTS

| | | | |
|---|---|---|---|
| 4,291,498 | 9/1991 | Janick et al. | 47/58 |
| 4,670,392 | 6/1987 | Cooley et al. | 435/240.4 |
| 4,672,035 | 6/1987 | Davidonis et al. | 435/240.4 |

OTHER PUBLICATIONS

Novak, et al (1986) in Proc. Int. FAO/IAEA Symposium, "Nuclear techniques and in vitro culture for plant improvement," IAEA, Vienna, pp. 443–449.
Hartmann, et al. Plant Propagation, principles and practices, Prentice–Hall, Inc, Englewood Cliffs, N.J., 1983, 444–445.
Ammirato in Handbook of Plant Cell Culture, vol. 1, Evans, et al, eds., MacMillan, N.Y., 1983, pp. 82–123.

*Primary Examiner*—Che S. Chereskin
*Attorney, Agent, or Firm*—Pennie & Edmonds

[57] ABSTRACT

The present invention provides a method for regeneration of somatic embryos from non-zygotic or zygotic tissue. The invention also provides a means for regeneration of cacao plantlets and plants from somatic embryos.

32 Claims, 22 Drawing Sheets

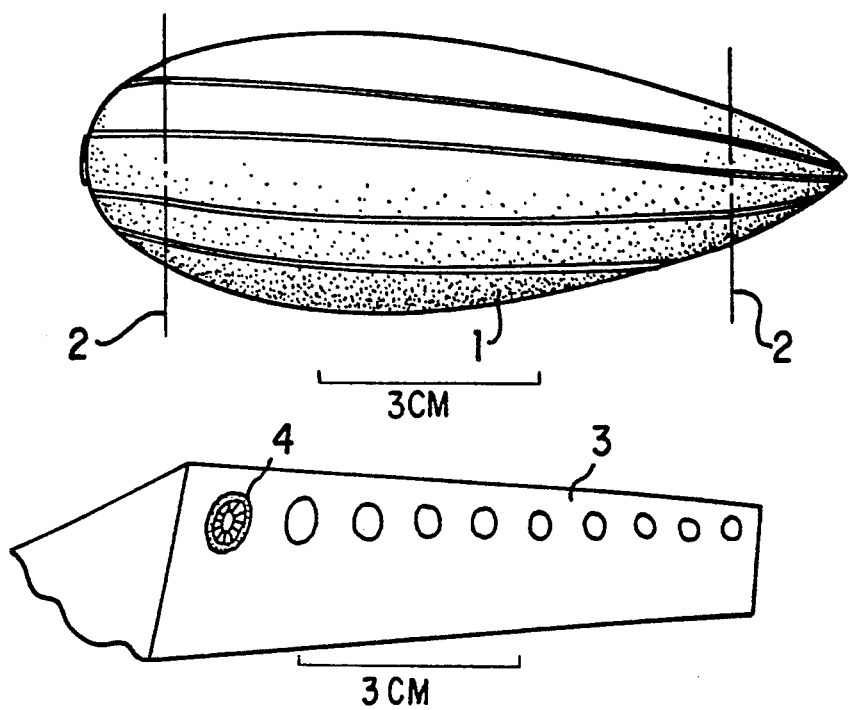
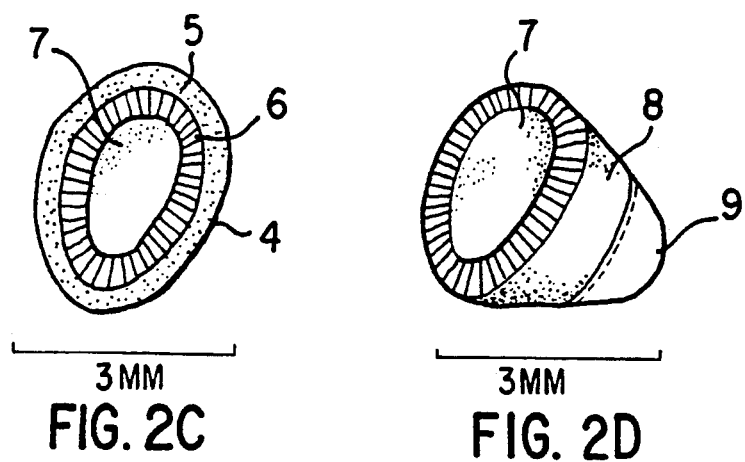

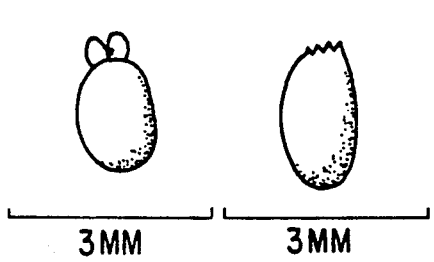
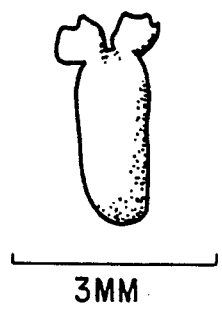
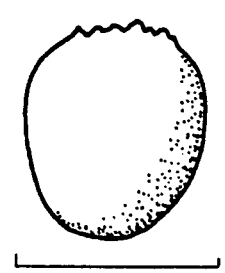
| 3MM | 3MM | 3MM | 3MM |
| --- | --- | --- | --- |
| FIG. 4A | FIG. 4B | FIG. 4C | FIG. 4I |
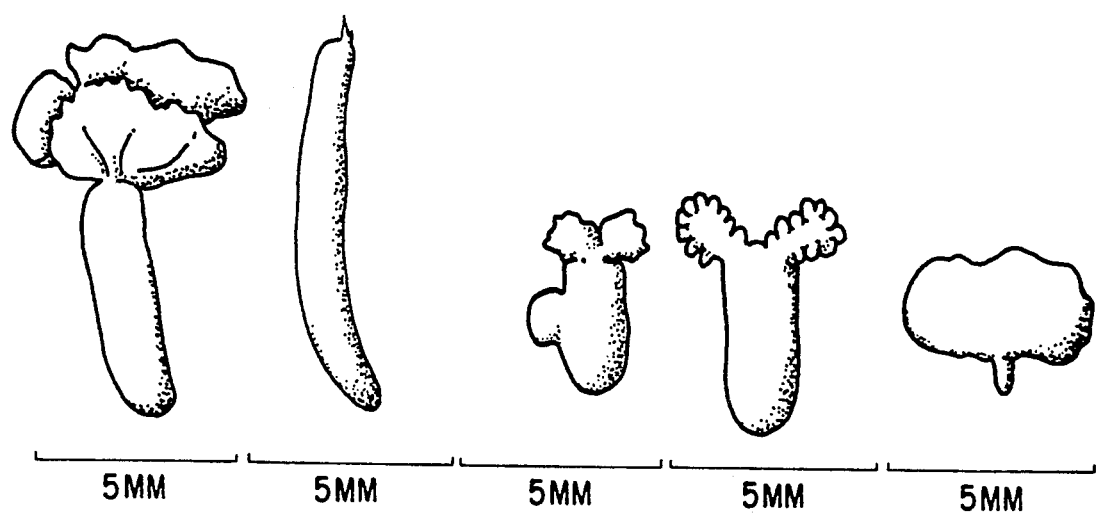
| 5MM | 5MM | 5MM | 5MM | 5MM |
| --- | --- | --- | --- | --- |
| FIG. 4D | FIG. 4E | FIG. 4F | FIG. 4G | FIG. 4H |

SOMATIC EMBRYOGENESIS AND PLANT REGENERATION OF CACAO

This application is a continuation-in-part of copending U.S. application Ser. No. 07/419,296, filed Oct. 10, 1989, now abandoned, which is a continuation-in-part of U.S. application Ser. No. 07/043,864, filed Apr. 29, 1987, now abandoned, the entire contents of each of which are incorporated herein by reference.

1. FIELD OF THE INVENTION

This invention relates to the field of improved techniques for the propagation of agricultural crop species. More specifically, the invention provides a method for the induction of in vitro embryogenesis from cacao somatic tissue of known genotype and the regeneration of plantlets, mature plantlets and mature plants therefrom.

2. BACKGROUND OF THE INVENTION

Complete in vitro plant regeneration capabilities provide highly desirable systems for the propagation of crop species. In addition, these same regeneration methods can be used to recover mature and reproductively fertile cacao trees from cacao cells which have undergone any of numerous techniques employing modern biotechnology. In particular, methods involving manipulation of plant cells in vitro require an efficient regeneration method. Cellular manipulation of cacao cells include, but are not limited to, gene transfer, gene deletion, in vitro selection, cell fusion and other techniques commonly practiced by biotechnologists.

It is advantageous to begin with a plant of a known phenotype and/or genetic composition. Typically, this plant will have desirable agronomic traits such as high yield, disease resistance, stand establishment etc. or some unique quality such as unique color, flavor, food quality, etc. For plant regeneration to be effective for cloning, a plant of a known phenotype must be faithfully reproduced as a copy of the original. For use of plant regeneration in modern biotechnology, limited gene or trait changes are typically sought in plants having a known and previously characterized phenotype. Therefore, an effective plant regeneration method must begin with plant material (explant) of a known genetic constitution and result in the development, from cell culture, of plants which mature and are capable of sexual reproduction.

Investigations concerning the morphogenesis of plant tissue in culture date back at least to the 1950's (Skoog, F. and Miller, C. O., Symp. Soc. Exp. Biol., 11:118 (1957)) and have continued apace to date. Several monographs provide extensive reviews of the field and contain compilations of numbers of species which will undergo plant regeneration in culture (see for example, Murashige, T., In: "Propagation of Higher Plant Through Tissue Culture," T. A. Thorpe, ed., p. 15, Univ. Calgary Press, Calgary (1978); Vasil, I. K. et al., Adv. Genet. 20:127 (1979) and Evans, D. A., et al. In: "Plant Tissue Culture: Methods and Applications in Agriculture", T. A. Thorpe, ed., p. 45, Academic Press, New York (1981)).

The impressive list of plant species cited in the above-referenced monographs, for which successful regeneration has been achieved, belies the difficulties in achieving those results. Successful regeneration of a particular species is often characterized by the addition of (or even omission of) catalytic amounts of auxins, cytokinins, or other growth regulators, proper inorganic and organic salt composition, frequency of subculture, choice of tissues, and physical growth conditions. Further, successful regeneration may also be a function of not only the mere presence of a certain compound but its ratio to other media components as well. Since each plant species and sometimes varieties within a species appears to possess a unique optimal set of media requirements, the successful preparation and regeneration of a new species cannot be necessarily inferred from the successful regimens applied to unrelated plant species.

Despite the recent advances in plant regeneration for a variety of species, cacao (*Theobroma cacao*) is one of the crops which has been refractory to regeneration protocols from non-sexual tissues and subsequent somatic embryo germination and plantlet development; hence, the application of plant cell culture for improvement of this crop has lagged behind that progress in the field in general.

Absent a functioning regeneration protocol, more traditional avenues for crop improvement have been utilized. One approach has been to introduce into the commercial cacao genome agronomically useful characteristics derived from exotic or "wild" *Theobroma cacao* germplasm by conventional sexual hybridization and backcrossing breeding procedures.

Attempts to culture plant cells progressed from studies to induce callus formation to more sophisticated studies to regenerate plants from cell culture.

Initial investigations relating to the tissue culture of *Theobroma cacao* demonstrated that it was possible to obtain callus from somatic tissue with relative ease. In fact, an early report (Archibald, J. F., Nature 173:351–352 (1954)) disclosed that it was possible to obtain callus from bark or stem explants on a White's basal culture medium without any growth regulators. Longer term sustained culture of the callus did, however, require a more complex medium. In retrospect the ease of callus formation has in fact been an obstacle rather than an advantage. Cacao's tendency to form unorganized growth in culture has heretofore frustrated attempts to successfully regenerate plants in the cacao system since tissue organization in the form of organs and/or embryos is often a prerequisite for plant regeneration.

Another approach has been described by E. B. Esan (In: Proceedings Fifth Int'l. Conf. on Cacao Research, Ibadan, Nigeria, pp. 116–124 (1975)) and (Kong and Rao, In: COSTED Symp. on Tissue Culture of Economically Important Plants, Singapore, 1981, Ed. A. N. Rao). According to these methods, embryos can be obtained through budding of cotyledon and hypocotyl tissue of young zygotic embryos. Since there are no known inbred cacaos and since these authors used zygotic embryos as the explant source, the cells they used were of an unknown genetic complement. Attempts to recover complete plantlets and plants from these zygotic embryos were a failure.

Employing a somewhat similar approach, Janick et al (U.S. Pat. Nos. 4,204,366; 4,291,498; 4,301,619 and 4,545,147) disclose methods for the induction of embryos of cacao from seed embryo cultures. Wang and Janick (Hort. Science 19:839–841) also described precocious germination of cacao embryos, but were unable to obtain mature plantlets and plants from them. In the cases above, the starting material used to initiate the embryogenesis protocol was zygotic embryo tissue, and therefore, cells were of unknown genetic composition.

Novak et al. (1986, in Proc. Int. FAO/IAEA Symposium, "Nuclear Techniques and In Vitro Culture For Plant Improvement," IAEA, Vienna, pp. 443–449) disclose again the use of zygotic seed embryos as an explant source to generate somatic embryos and to recover germinated cacao embryos and early stages of plantlet development. Novak et al. used "maturation medium" to attempt to develop cacao plantlets after embryo germination. No attempt was made to use non-zygotic explant sources to obtain somatic embryos for micropropagation purposes. Novak et al. further disclose the use of a "cotyledon", a zygotic tissue to generate somatic embryos.

Several attempts have been made to regenerate cacao from somatic tissues of known genotype. Attempts to culture terminal or auxiliary buds were reported by Orchard et al., 1979 (Physiol. Plant 47:207–210). Although some bud swelling and leaf elongation were reported, the regenerative propagation of intact plants was unsuccessful.

In another report, Litz ("Tissue Culture Studies with *Theobroma cacao*," Proc. Symp. Cacao Biotech., P. S. Dimick (ed.), pp. 111–120, 1986) does describe the early phases of development of somatic embryos from mature somatic (leaf) tissue; however, all attempts to complete embryo development and recovery of plantlets have also proven futile.

The somatic embryogenesis in cacao discussed above, relies on either tissue from immature sexual embryos, and thus the genetic origin of the somatic embryos is also unknown or, where somatic explant tissue is used, there has been a failure to regenerate a mature reproductively competent cacao plant.

3. SUMMARY OF THE INVENTION

The present invention provides a method which initiates cacao plant cell cultures from a donor explant of a known phenotype and genetic composition. The present method also provides a method for regeneration of somatic embryos from said cell cultures. The invention further provides methods for the development of the somatic embryos into germinated embryos, plantlets and mature plants. The ability to regenerate plants from maternal somatic tissue is extremely useful in any form of breeding strategy in which knowledge of the genotype of progeny is critical to its success. For example, somatic embryogenesis from maternal somatic tissue, which ultimately results in plant production, is an important step in applying large scale vegetative propagation to selected donor plants in the field, and for development of selected parents for hybrid seed production. It is also a useful step in production of somaclones, in vitro selection of mutants, protoplast isolation, and DNA uptake via protoplasts or directly via microinjection or electroporation.

The present invention relates to a method for producing a mature cacao plantlet, which itself is capable of growing into a mature cacao plant, which comprises:
(a) providing a cacao somatic embryo;
(b) culturing the somatic embryo on a differentiation medium to obtain differentiation of the embryo; and
(c) germinating the differentiated embryo on a germination medium to produce a mature cacao plantlet.

The differentiation medium in one embodiment preferentially comprises an osmoticum and/or growth regulator(s). A preferred growth regulator is abscisic acid. The differentiation medium may also optionally include other growth regulators such as a gibberellin(s) (e.g. gibberellic acid), a cytokinin(s), and/or an auxin(s). In another embodiment, the somatic embryo is cultured on a differentiation medium under conditions of dehydration. Such differentiated embryos develop into plantlets, and further, into mature plants that have normal flowers and fruits.

The invention also relates to a method of obtaining a somatic embryo from non-zygotic somatic tissue of a mature cacao plant which comprises:
(a) culturing said non-zygotic somatic cacao tissue on a primary culture medium comprising effective amounts a growth regulator to obtain an immature embryo; and
(b) culturing the immature embryo in a regeneration medium comprising effective amounts of a growth regulator to complete the development of a cacao somatic embryo.

The foregoing method is particularly well adapted to development of embryos from nucellus and young petal tissue. In one embodiment of the invention, the primary culture medium and/or the regeneration medium may further comprise an osmoticum.

The present invention is the first demonstration of successful regeneration via somatic embryogenesis of cacao plants from explant tissue of a known phenotype and genetic source The advantage of the methodology described in the following section is that it is capable of producing genetic carbon copies, or clones, of a known donor plant which has been selected under field conditions, in light of its superior qualities. A further advantage of the present invention is that the method can be utilized in numerous modes to effect genetic modification of cacao using modern biotechnology.

| 3.1. ABBREVIATIONS | |
|---|---|
| ABA- | (±) cis-trans-Abscisic Acid |
| 6-BA- | 6-Benzylaminopurine |
| CW- | Coconut water |
| 2,4-D- | 2,4-Dichlorophenoxyacetic Acid |
| FET- | Friable embryonic tissue |
| GA- | Gibberellic Acid |
| IAA- | Indole-3-Acetic Acid |
| 2-iP- | 2-isopentenyl adenine |
| KIN- | Kinetin |
| MES- | 2-[N-Morpholino]ethanesulfonic Acid |
| NAA- | α-Naphthaleneacetic Acid |
| PBP-40- | Polyvinylpyrrolidone (Mol. Wt. 40,000) |
| MS- | Murashige & Skoog medium |
| KAO's- | Kao & Michayluk Medium |
| SE- | Somatic Embryo |
| WPM- | Woody Plant Medium |
| ZEA- | Zeatin |

3.2. DEFINITIONS

As defined herein, a "plantlet" is a young plant derived from the somatic embryogenesis process. After germination of a somatic embryo, the plantlet, while still in medium, undergoes a vegetative growth that is characterized by the development of several new leaves, epicotyl and hypocotyl elongation, and branching of the root system. A plantlet of ca. 40 mm in length containing at least 4–5 true leaves is transferred to soil under hardening conditions (high moisture, low light intensity, controlled temperature).

As defined herein, a "mature plantlet" is one which has active growth in a vessel containing soil characterized by elongated hypocotyl and epicotyl, with the presence of roots, primary leaves, and an active apical meristem.

As defined herein, a "mature plant" is one which is capable of producing flowers and fruits.

As defined herein, "nucellus" refers to a maternal ovary tissue that nurtures the embryo sac development. Young flower bud petals are modified leaf structures that protect the reproductive parts of a flower bud.

As defined herein, "young petals" and "young flower buds" are derived from unopened buds, usually about 5-8 mm in length; the preferred petals are generally about 3-5 mm in length.

4. BRIEF DESCRIPTION OF THE FIGURES

FIG. 1 shows a flow diagram for the production of cacao plantlets via somatic embryogenesis derived from non-sexual explant tissues.

FIG. 2 shows a schematic representation of young pod sectioning and isolation of nucellus explants. FIG. 2A shows a side view of a young fruit. FIG. 2B shows a perspective view of a quarter section of a young fruit. FIG. 2C shows a cross-section view of an immature seed. FIG. 2D shows a perspective view of a cross-section of an immature seed. A young fruit, shown before cutting (1) has both ends cut (2). A section (one quarter) of the fruit (3) includes several immature seed cavities (4). A seed coat (5) has inside it nucellus tissue (6) and a cavity containing liquid endosperm (7). A nucellus explant isolated from the seed coat (8) has a lower extremity (9) which is cut off to eliminate the zygotic embryo.

Figure 3A:
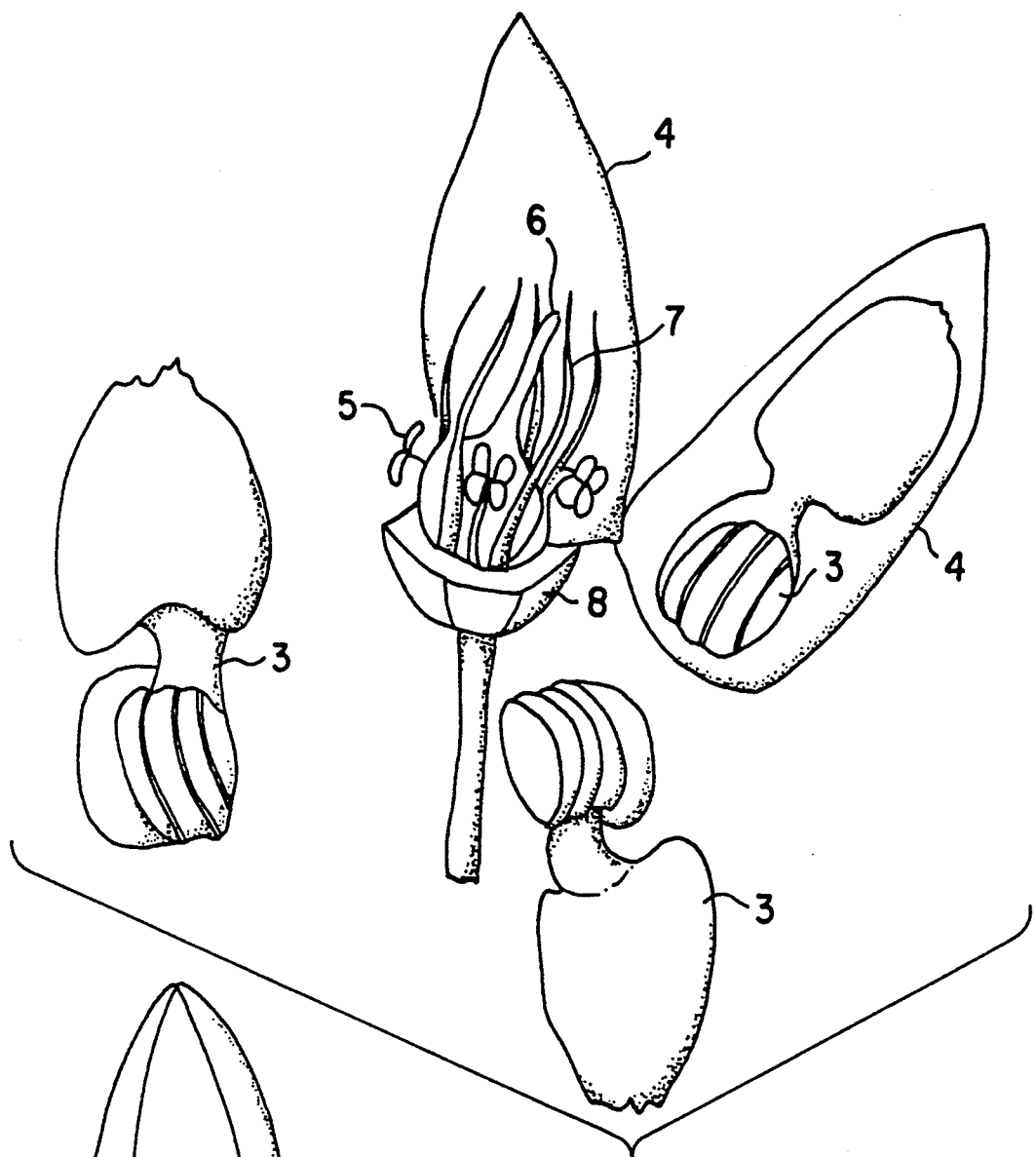
Figure 3B:
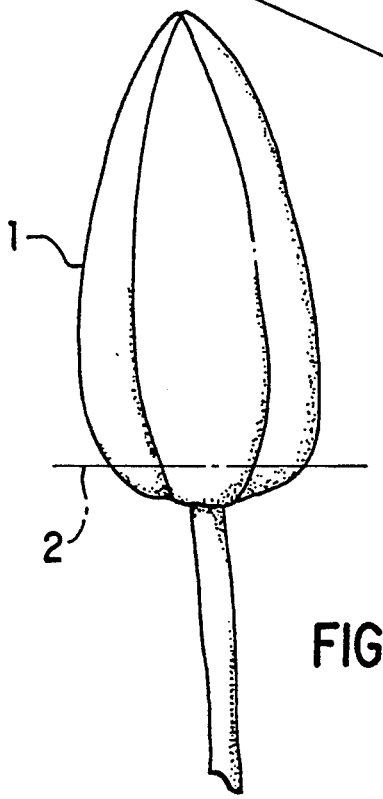
Figure 5A:
Figure 5B:
Figure 5C:
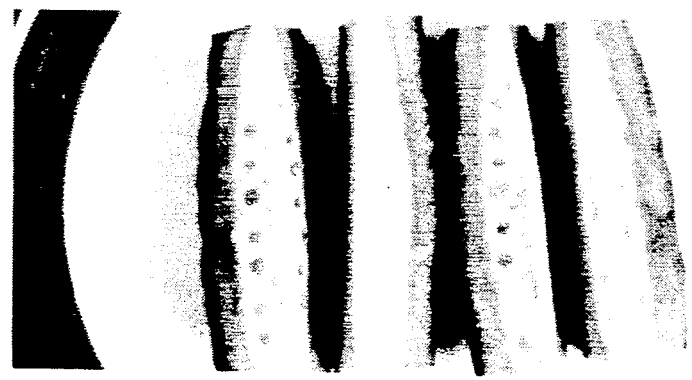
Figure 5D:
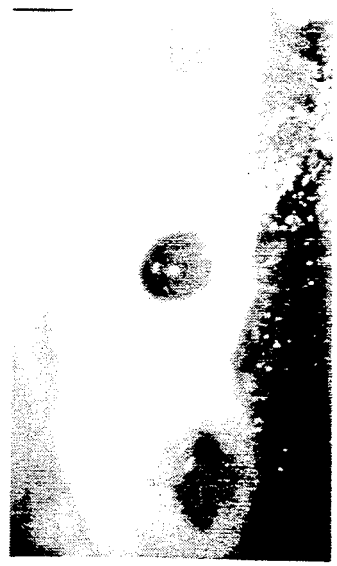
Figure 5E:

FIG. 3 shows a schematic representation of a young flower bud and the excision of petal explants. FIG. 3B shows a side view of an intact young flower bud. FIG. 3A shows an exploded view of the flower parts released from a young flower bud resulting from a planar cut through the line indicated by 2 in FIG. 3B. An intact young flower bud (1) is cut along line 2 to excise the petal explants. The isolated petal explant (3) before culture is shown. 4 is an illustration of the presence of five sepals, also showing five anthers (5) and respective filaments, the ovary (6) and five Stamnode (7). The remaining portion of the flower bud after cutting is also illustrated (8).

FIG. 4 shows a schematic representation of 'normal' (A-E) and abnormal (F-I) cacao somatic embryos observed in the regeneration medium. FIG. 4A shows the late globular or heart shape stage. FIG. 4B shows the early torpedo stage embryo before cotyledon development. FIG. 4C shows the late torpedo stage embryo with developing cotyledons. FIG. 4D shows a somatic embryo with the presence of large cotyledons. FIG. 4E shows elongated somatic embryo without cotyledons. FIG. 4F shows young somatic embryo with secondary embryo differentiation. FIG. 4G shows torpedo stage embryos with proliferation of embryogenic tissue from cotyledonary leaves. FIG. 4H shows abnormal embryo with aborted hypocotyl and oversize cotyledons. FIG. 4I shows very large globular structure that does not follow normal embryo development.

FIG. 5 shows photographs of steps involved in obtaining nucellus explants. FIG. 5A shows young cacao fruit with ca. 100 mm in length and 33 mm in width (Magnification=1.1×). FIG. 5B shows young cacao fruit after cutting off the two ends (Magnification=1.0×). FIG. 5C shows longitudinal sections of young cacao fruit before nucellus explant excision (Mag=1.0×). FIG. 5D shows a close-up of immature seed cavities from one longitudinal section containing nucellus tissue and liquid endosperm (Magnification=6.7×). FIG. 5E shows examples of excised nucellus explants, without seed coat (top) and with seed coat (bottom) (Magnification=16.7×).

Figure 6A:
Figure 6B:
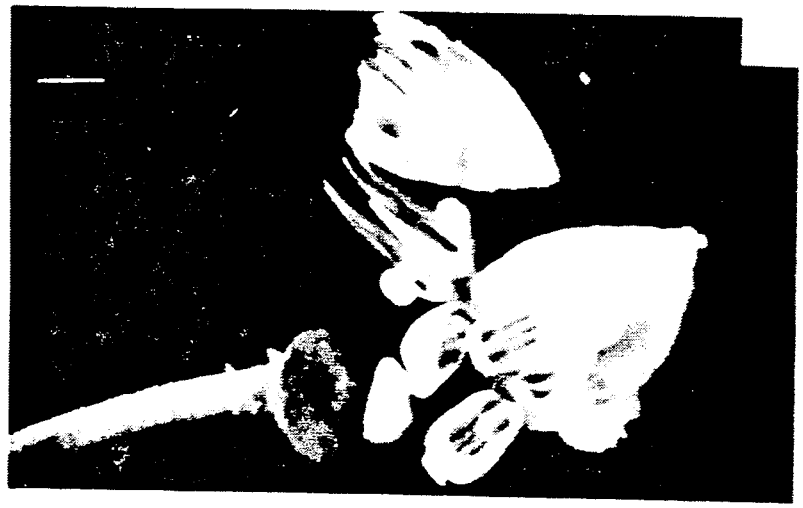
Figure 6C:
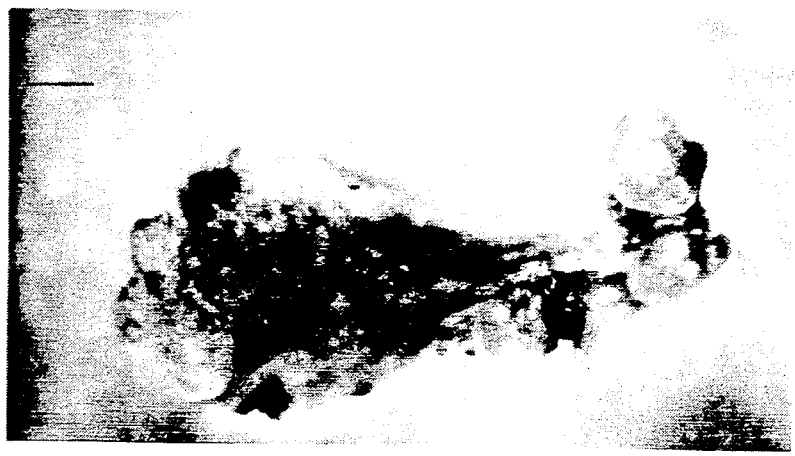
Figure 7A:
Figure 7B:
Figure 7C:
Figure 7D:

FIG. 6 shows photographs of steps involved in obtaining petal explants. FIG. 6A shows an illustration of three developmental stages of cacao flower buds. Petal explants are taken from the small and medium size buds (Magnification=6.7×). FIG. 6B shows a dissected cacao flower bud illustrating the presence of calyx base, sepals, petals, anthers and ovary (Magnification=7.7×). FIG. 6C shows young petal explant with callus growth after 4 weeks in culture (Magnification=2.5×).

FIG. 7 shows photographs of somatic embryo regeneration. FIG. 7A shows primary somatic embryos from nucellus explants after 4 weeks on primary culture medium (Magnification=50×). FIG. 7B shows embryogenic tissue derived from primary embryo explant after 3 weeks in regeneration medium (Magnification=14×). FIG. 7C shows secondary embryo differentiation from embryogenic tissue after 6 weeks on regeneration medium. FIG. 7D shows ivory and translucent secondary embryos isolated from regeneration medium at different stages of differentiation (Magnification=9×).

Figure 8A:
Figure 8B:
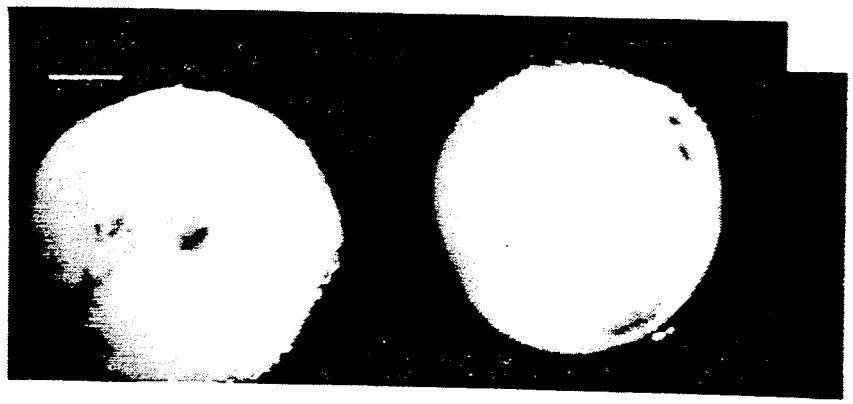
Figure 8C:
Figure 9A:
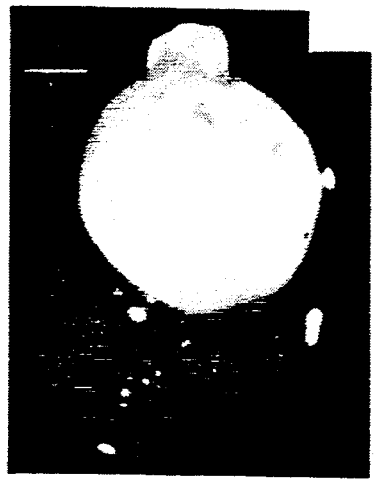
Figure 9B:
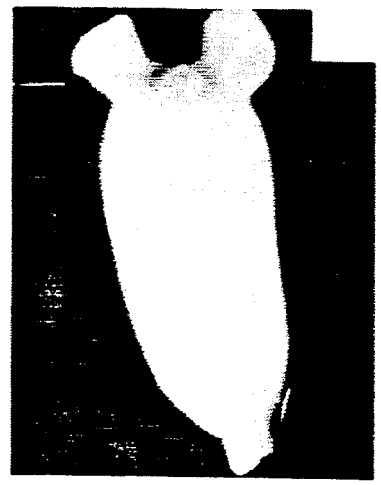
Figure 9C:
Figure 9D:

FIG. 8 shows photographs of normal and abnormal embryos from nucellus or petal explants. FIG. 8A shows an illustration of two normal somatic embryos at early stage of differentiation (Magnification=25×). FIG. 8B shows oversized abnormal somatic embryos at the globular stage. These embryos regularly failed to follow the normal sequence of development (Magnification=25×). FIG. 8C shows an example of one abnormal embryo (left) and one normal embryo (right) isolated from the same culture. The abnormal embryo is characterized by overexpanded cotyledonary leaves and very short hypocotyl axis. These abnormal embryos fail to produce an elongated hypocotyl and to follow normal germination (Magnification=20×).

FIG. 9 shows photographs of somatic embryo development from nucellus or petal explants. FIG. 9A shows the globular stage of cacao somatic embryo at the early stage of cotyledonary leaf differentiation after 6 weeks of culture on regeneration medium (Magnification=33×). FIG. 9B shows the torpedo stage of cacao somatic embryo after 6 weeks of culture in the regeneration medium (Magnification=20×). FIG. 9C shows the cotyledonary stage of cacao somatic embryos after 2 weeks in early differentiation medium. (Magnification=9×). FIG. 9D shows fully developed cacao somatic embryo after 8 weeks in late differentiation medium. (Magnification=10×).

FIG. 10 shows the germination, hardening, and plant establishment in soil. FIG. 10A shows a germinating cacao somatic embryo after 5 weeks in germination medium. Germinated embryos have elongated hypocotyl and epicotyl and several primary leaves. (Magnification=1.0×). FIG. 10B shows plantlet development of cacao somatic embryo after 8 weeks in solid culture (Magnification=1.0×). FIG. 10C shows a mature cacao plantlet derived from nucellus somatic embryo after 5 weeks in the hardening conditions (Magnification=0.7×). FIG. 10D shows a mature cacao plantlet derived from nucellus somatic embryo after 8 weeks in soil under shaded greenhouse conditions (Magnification=0.4×). FIG. 10E shows cacao plants derived from nucellus somatic embryo after 16 months in normal greenhouse conditions. (Magnification=0.08×).

Figure 10A:
Figure 10B:
Figure 10C:
Figure 10D:
Figure 10E:
Figure 10F:

FIG. 10F shows a cacao fruit and a flower bud on a mature cacao plant.

Figure 11A:
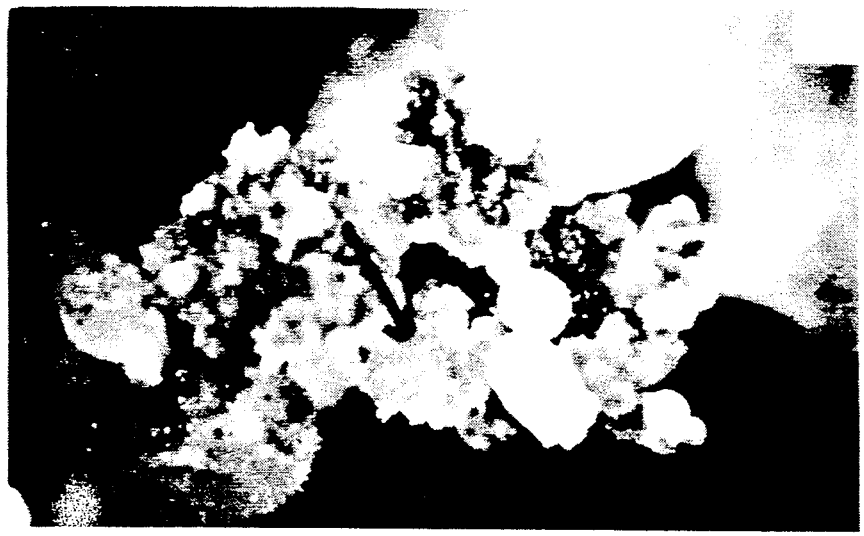
Figure 11B:
Figure 11C:

FIG. 11 shows the establishment of cacao embryogenic cell suspension. FIG. 11A shows friable embryogenic tissue (FET) induced on a solid Multi-V medium. FET colonies were used to establish the coarse cell suspension cultures of cacao (Magnification=20×). FIG. 11B shows established cell suspension of cacao in 125 ml flask showing different multiplication stages of FET (Magnification=3 X). FIG. 11C shows a close up of one suspension flask illustrating the coarse nature of the suspension (Magnification=1 X).

Figure 12A:
Figure 12B:
Figure 12C:
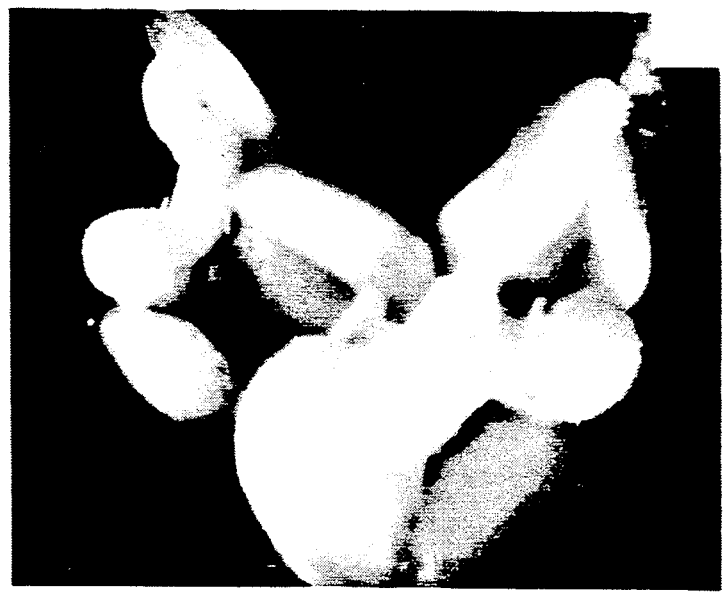

FIG. 12 shows regeneration of somatic embryos from cacao embryogenic suspension cultures. FIG. 12A shows newly plated aggregates from cacao suspension cultures on a solid regeneration medium (Magnification=30 ×) FIG. 12B shows embryo regeneration on solid regeneration medium (Magnification=20×). FIG. 12C shows embryo regeneration after 6 weeks of plating on solid regeneration medium; note some well developed somatic embryos at the torpedo stage (Magnification=20×).

5. DETAILED DESCRIPTION OF THE INVENTION

On their face, the principles underlying plant tissue culture are quite simple. Initially, it is necessary to isolate a plant part from the intact plant and disrupt its organ, inter-tissue, or inter-cellular relationships. Subsequently, it is necessary to provide the isolated explant with the appropriate environment in which to express its intrinsic or induced developmental potential. Finally, all these steps must be carried out aseptically. Although the principles may be simply stated, as a matter of practice, the successful culture of plant tissues and their production into a mature plantlet and mature plant is extremely complex.

5.1. PRODUCTION OF A SOMATIC EMBRYO

There are two general patterns of in vitro embryogenesis: direct initiation from differentiated tissue, and indirect initiation via a callus intermediary. Direct embryogenesis proceeds from embryogenically-determined cells. Indirect embryogenesis requires dedifferentiation of cacao cells, callus proliferation, and differentiation of embryogenic cells.

Plant regeneration via a callus intermediary first involves the transfer of an explant onto a culture medium to stimulate the proliferation of the explant or callus. This is followed by a rapid increase in embryo differentiation and organ growth and may require a transfer to a second medium with or without a change in growth regulator concentration. In vitro plantlets are removed from in vitro culture and requires the establishment of the autotrophic state.

A number of experimental parameters must be addressed during this protocol. For example, for a particular species, the source of the explant may be important for the success of the subsequent regeneration. The size and the shape of the explant may also be important. Another element to be considered is the method of providing aseptic explant material for purpose of callus formation. This involves sterilization of the explant tissue prior to inoculation onto medium. Even this apparently routine process is subject to a wide variety of experimental parameters.

The present method can be employed to obtain whole cacao plants from somatic embryos from any source, including but not limited to zygotic embryos, zygotic tissue, seeds or seed pieces, hypocotyls, and cotyledons, although, embryos derived from mature somatic tissue is preferred. In this vein, the present invention also provides a novel method for obtaining somatic embryos from somatic tissues of mature cacao donor plants. The present method has proven useful in the development of somatic embryos from two new sources of somatic tissues, namely nucellus and young flower bud petals. This method has proven particularly useful in combination with the foregoing differentiation and germination procedures for permitting the production of mature cacao plantlets and subsequent mature cacao plants. However, the procedure may also be used in any situation in which production of somatic cacao embryos are expected to be useful.

Two phases characterize the method for obtaining a somatic embryo from non-zygotic tissue. During the initial or inoculation phase, the development of immature somatic embryos is obtained by culturing explants of nucellus, or young petals, in a primary culture medium containing at least one growth regulator, either a cytokinin or an auxin at concentrations sufficient to initiate embryo development. Such primary culture medium may also be referred to as primary culture medium (see Section 9, infra). The cytokinin may be selected from the group including but not limited to zeatin, 2-iP, 6-BA, zeatin, or kinetin and may be present at for example, concentrations up to about 20 $\mu$M and preferably from about 1 to about 5 $\mu$M. The auxin may be selected from the group including but not limited to 2,4-D, indole-3-propionic acid, indole-3-butyric acid, indole-pyruvic acid, phenylacetic acid, phenoxyacetic acid, naphthoxyacetic acid, naphthalene acetic acid, and indole acetic acid at concentrations, for example, up to about 10 $\mu$M. The primary culture medium is also supplemented with coconut water, an element frequently used in the art in embryogenic medium, in an amount of about 25-100 ml/l of medium. The remaining components comprise a basal medium (see, e.g., *Handbook of Plant Cell Culture*, Evans et al., Vol. I, 1984) consisting essentially of basal inorganic salts being present in the amount of about 0.1-1.0 X; and a source(s) of organic nitrogen, such as casein hydrolysate and/or individual amino acids The primary culture medium may optionally comprise an osmoticum (e.g. sucrose). When sucrose is employed, the amount is generally about 80-140 g/l of medium. This provides an osmotic potential in the range of −5.8 bars to −10.1 bars. However, it is also possible to substitute other sugars or sugar alcohols, such as glucose, mannitol or sorbitol to obtain equivalent osmotic effects.

The primary culture medium may be solidified with agar, or another gelling agent, or may be a liquid medium, and the cultures maintained in the dark at a temperature of about 24°-28° C. for about 45 days, or until immature somatic embryos, typically globular or heart-shaped, appear in the callus mass.

During the regeneration phase, immature embryos are transferred to a second medium, the regeneration medium. The presence of specific growth regulator(s) in this medium is essential to the successful completion of embryo development. In one embodiment, the growth regulator is an auxin, e.g. NAA, up to about 10 $\mu$M. In another embodiment, the growth regulator is cytokinin, having a concentration of about 0.5 $\mu$M to about 15 $\mu$M. The preferred cytokinin is zeatin, if the explant source is nucellus, but this may also be combined with kinetin or another cytokinin. If the explant source is petal tissue, the preferred cytokinin is 6-BA. The medium may also contain a gibberellin (e.g. gibberellic acid) and ABA, in concentrations of about 0.3-1 μM and 0.01-0.07 μM, respectively.

The remainder of the regeneration medium composition is, as with the primary culture medium, not restricted to any particular composition. Again, salts are preferred being present in an amount of about 0.1-1.0 X. Additional sources of vitamins, nitrogen and carbon are also typically present. Coconut water may be used to provide a convenient source of many of these elements. Sucrose is the preferred carbon source, in an amount of about of about 25-40 g/l; however, sucrose may be replaced by similar quantities of glucose or a 1:1 mixture of fructose to glucose. The pH is preferably maintained in a range of about pH 5-6. The embryos are incubated on the solidified or liquid regeneration medium at a temperature of about 24°-28° C., under low light (300-1000 lux, preferably 300-400 lux) conditions or in the dark for a period of about 25-40 days; a 30-day period appears to be optimal. As an optional element in this regeneration phase, the developing embryos may be periodically transferred to new media with a progressive increase in the amounts of cytokinin and gibberellin in the new medium. Alternatively, the developing embryos may be transferred to a secondary medium comprising a cytokinin for several months in the dark.

In one embodiment of the invention, the isolated somatic embryos may be used as an explant source for secondary embryo production on regeneration medium, which comprises effective amounts of growth regulator(s) to stimulate secondary embryo production. In a preferred embodiment, the regeneration medium comprises at least one growth regulator, as with the primary culture medium. The remainder of the regeneration medium composition is, as with the primary culture medium, not restricted to any particular composition. Again, salts are preferred being present in an amount of about (0.1-1.0 X). Additional sources of vitamins, nitrogen and carbon are also typically present. Coconut water may be used to provide a convenient source of many of these elements. Sucrose is the preferred carbon source, in an amount of about of about 25-40 g/l; however, sucrose may be replaced by similar quantities of glucose or a 1:1 mixture of fructose to glucose. The pH is preferably maintained in a range of about pH 5-6. The embryos are incubated on the solidified regeneration medium or liquid regeneration medium at a temperature of about 24°-28° C., under low light (300-1000 lux, preferably 300-400 lux) conditions or in the dark for a period of several months.

In one specific embodiment, the explant may be cultured on a solid primary culture medium described above. Friable embryogenic tissue is subsequently suspended in a liquid medium comprising at least one growth regulator, preferably a cytokinin preferably having a concentration from about 0.5 μM to about 10 μM for several months in the dark. The suspended embryogenic aggregates are subsequently cultured on a solid regeneration medium described, supra.

In another specific embodiment, the explant may be cultured on a solid primary culture medium described above Friable embryogenic tissue is subsequently suspended in a liquid regeneration medium comprising at least one growth regulator, preferably a cytokinin preferably having a concentration from about 0.5 μM to about 10 μM for several months in the dark.

Whichever procedure is followed, at the end of the regeneration phase, the embryos are ready to be transferred to a differentiation medium, or to be used in any other procedures for which somatic embryos would prove useful.

5.2. DIFFERENTIATION

The present invention has succeeded in producing cacao plantlets and plants by virtue of the recognition that the cacao embryo requires a differentiation phase on a medium distinct from media used to generate the somatic embryo. Several previous methods have attempted plantlet and plant production by continued culturing of immature embryos on a primary culture medium. In fact, callus is extremely easy to develop from a variety of different organs or explants, on a wide range of culture medium. However, obtaining any further substantial differentiation, i.e., past the embryo stage, has proven difficult, if not impossible. Similarly, as in the case of Wang and Janick, cited supra, it was possible to initiate precocious germination in zygotic embryos, but still impossible to develop any actual plantlets from the germinated seedling. It has now been discovered to be extremely advantageous that the cacao embryos must be passed through a differentiation phase (referred to in application Ser. Nos. 07/043,864 and 07/419,296 as the maturation phase) in order to be capable of producing viable plantlets, subsequently, a normal germination process and ultimately plants. Passage through this differentiation phase appears to be very important in obtaining normal plantlets from somatic embryos, the distinct treatment being necessary to the normal differentiation of the embryo, i.e., formation of root and shoot meristematic regions.

The differentiation phase should preferably comprise at least two subphases, "early" and "late" in which the embryo is transferred to different differentiation media. Alternatively, the embryos during the differentiation phase may be successively transferred to fresh medium of the same type used at the start of the differentiation phase. During the early differentiation phase, the somatic embryo changes morphologically from a globular or heart shape to a torpedo shape. During the late differentiation phase, somatic embryos further develop the shoot and root meristems and allowances for the accumulation of storage systems and hypocotyl elongation.

The differentiation medium, preferably comprises abscisic acid at a concentration up to about 300 μM, preferably from about 100 to about 200 μM. The differentiation medium may optionally further comprise a cytokinin and a gibberellin, such as gibberellic acid. The cytokinin may be selected from the group including, but not limited to zeatin, kinetin, 6-BA, and 2-iP, present in amounts up to about 300 μM, preferably from about 25 μM to about 75 μM. Gibberellin, such as gibberellic acid, may be present in amounts up to about 15 μM, preferably from about 2.5 to about 7.5 μM.

The differentiation medium may also comprise an auxin. A number of different types of auxins are available, both natural and synthetic; among these are indole-3-propionic acid, indole-3-butyric acid, indolepyruvic acid, phenylacetic acid, phenoxyacetic acid, naphthoxyacetic acid, naphthalene acetic acid, and indole acetic acid. One of these compounds may be present in the differentiation medium, in an amount of about 0.5-2.0 μM total.

As mentioned supra, in one embodiment of the invention, the embryo after culturing in a first differentiation medium may be transferred to a second differentiation medium to obtain mature embryos. The second differentiation medium may comprise abscisic acid having a concentration up to about 15 μM, preferably 0.5–5 μM.

In addition to the growth regulators, the presence of sucrose or an equivalent sugar as osmoticum, as well as a nutrient source in the differentiation media, is also desirable. When sucrose is employed, the amount is generally about 80–140 g/l of medium. This provides an osmotic potential in the range of −5.8 bars to −10.1 bars. However, it is also possible to substitute other sugars or sugar alcohols for sucrose, such as glucose, mannitol or sorbitol to obtain equivalent osmoticum effects.

The foregoing elements are those which have an advantageous effect on the initiation of differentiation of the embryo. However, the differentiation medium will of course contain a number of elements which, while necessary for the normal growth and metabolism of the embryo, do not themselves effect differentiation. Obviously, it is necessary to have at least one exogenous nitrogen and carbon source, as well as desirable to have the preferred vitamins and salts, but the nature of the elements can vary as is understood in the art.

The basal medium from which the differentiation medium may be formulated from for example, Murashige and Skoog (MS) medium or Gamborg's B5 medium having a specific formulation of macro- and micronutrients, which formulations are well known in the art (see, e.g., *Handbook of Plant Cell Culture*, Evans et al., Vol. I, 1984). The particular concentration of the salts at this phase is not critical, but generally will typically be used in an amount of about 0.1–2.0 X of the mediums's original formulation. The presence of additional iron salts, such as MSV (Murashige and Skoog iron solution), are also important and preferably are added in an amount of about 0.1–2.0 X. Nitrogen sources may be provided by addition of individual amino acids, in the form of a protein hydrolysate such as casein hydrolysate (casein-HCl), or both. Various sources of carbon, other than the sugar used as osmoticum, may also preferably be added. A particularly useful source of a variety of complex sugars is malt extract, which also contains vitamins, minerals, amino acids, and hormones. Any convenient source of vitamins may also be employed. Agar may be added to solidify the medium, or the medium may be liquid, as may the subsequently used medium, and the pH is adjusted to about 4–5.5. Low light, i.e, from 300–1000 lux, is preferred, with 300–400 lux being most preferred. A visual indicator for the time of transfer of a fully mature embryo is the development on the embryo of a perceptible swelling at the site of the apical meristem, indicating shoot tip development. This can generally be readily observed with the aid of a low power magnifying glass or microscope. Root tip development is also helpful in gauging the time of transfer to fresh differentiation medium but is not as important as shoot tip development. However, this progressive transfer is by no means critical to the success of the differentiation stage. Alternatively, as detailed in Section 9, the embryos may be cultured on early differentiation medium until embryos reach 6–10 mm (approximately four weeks), then subsequently transferred to late differentiation medium for approximately eight weeks.

In another embodiment, the somatic embryo may be incubated in differentiation media which comprises a basal medium and an osmoticum providing an osmotic potential of at least about −7.0 bars, preferably ranging from about −7.0 bars to about −11.0 bars. In yet another embodiment, the somatic embryo may be incubated in an early differentiation medium comprising an osmoticum and a growth regulator, preferably abscisic acid, and is subsequently incubated in a late differentiation medium which comprises a basal medium and an osmoticum providing an osmotic potential of at least about −7.0 bars, preferably ranging from about −7.0 bars to about −11.0 bars.

In a further embodiment, differentiation may occur by incubating the somatic embryos in a basal medium under dehydration conditions. For example, somatic embryos can be placed on a 32 oz. jar with agar medium (SEVI A5 or LMI), covered with PVC film, and allowed to undergo a gentle dehydration under dark conditions.

5.3. GERMINATION

Germination may be obtained on a solid medium or liquid medium. The liquid germination medium may comprise at least one auxin, in an amount up to about 5 μM and a gibberellin, such as gibberellic acid, may be present in an amount of up to about 6 μM, preferably from about 1.5 μM to about 4.5 μM. The solid medium may comprise an auxin, e.g. IAA in an amount up to about 5 μM, preferably from about 2.5 μM to about 7.5 μM and a cytokinin, e.g. 6-BA, in an amount up to about 10 μM, preferably from about 2.5 μM to about 7.5 μM. In the germination medium, there is no longer a necessity for sucrose to be present in large amounts as osmoticum, although small amounts usually no more than about 4%, can remain as a source of energy. The remaining composition of the germination medium is essentially the same as described for the differentiation medium, i.e., a general mixture of nitrogen, carbon, and vitamin sources, with for example, 0.5–1.5 X salts (e.g. WPM salts, Lloyd and McCown, 1981, Int. Plant Prog. Soc. Proc. 30:421–427). The pH of the medium is preferably about pH 5–6. Light conditions are generally high, about 1000–3000 lux, with about 2500 being preferred. Germination normally occurs in about 20–35 days, resulting in plantlets.

5.4. PLANTLET AND PLANT PRODUCTION

After germination, plantlets may be transferred to fresh germination medium, or alternatively to a new medium comprising reduced strength salts and a growth regulator to further plantlet growth (development phase). The fully developed plantlets, during the subsequent transplanting phase are transferred to soil for the plantlets to harden and become mature plantlets.

Alternatively, plantlets after developing an elongated hypocotyl and 2–3 true leaves before transferring to soil, may be transferred to a "hardening box" Such a box is covered with, for example, PVC film and air is pumped through in a controlled fashion. The plantlets transferred to the hardening box are also covered. The air flow into the box is increased over time. Additionally, the plantlets are gradually uncovered.

Mature cacao plants are obtained after mature plantlets are transferred to larger pots and allowed to complete vegetative growth up to flowering and fruit setting. Alternately, mature cacao plants can be obtained by grafting a differentiation phase somatic embryo as scion onto young cacao seedling root stock.

The foregoing procedures have been successful in producing mature plantlets and plants from embryos of a variety of different cacao genotypes; mature plants have also been obtained by grafting of plantlets to seedling root stock. Although the optimal composition of the medium may differ for each genotype, the general compositions outlined above routinely produce mature plantlets. The minor modifications of the nonessential components of the minor modifications of the nonessential components of the medium which may be necessary to optimize yield are well within the skill of the experienced worker, without the necessity for undue experimentation.

Specific description of applications of both the somatic embryogenesis procedure and the further development of mature plants from somatic embryos, are presented in the following non-limiting examples.

6. EXAMPLE 1: PROTOCOL FOR SOMATIC EMBRYOGENESIS, EMBRYO GERMINATION, PLANTLET DEVELOPMENT, AND HARDENING

Young cacao fruits measuring 60–100 mm long have yielded the best nucellus explants for callus induction and regeneration. Fruits were split in half after surface sterilization with 80% ethanol and 2.1% sodium hypochlorite. Nucelli were isolated from immature seeds, cut into small segments, and placed on primary culture medium. The basal end of the nucellus was always eliminated to avoid the presence of sexual embryo tissues.

6.1. PRIMARY CULTURE

Segments of nucellus tissue are inoculated on primary culture medium. The composition of this medium is as follows: half concentration of Murashige and Skoog (MS) inorganic salts, thiamine (30 $\mu$M), pyridoxine (15 $\mu$M), nicotinic acid (15 $\mu$M), glycine (5 mg/l), cysteine (200 mg/l), casein hydrolysate (50–100 mg/l), malt extract (100–500 mg/l), polyvinylpyrrollidone (PVP) (5–10 g/l), coconut water (50–100 ml/l), sucrose (20–40 g/l), 2,4-dichlorophenoxyacetic acid (0.5–3.0 mg/l), 2-iP (2.5 $\mu$M), agar (7 g/l) or GELRITE (2.3 g/l), pH 5.3. The medium is then autoclaved. Primary cultures are maintained at 24°–28° C. temperature under dark conditions.

6.2. REGENERATION

Early somatic embryos arising on the primary culture medium are isolated from callus mass and explant pieces and transferred onto a regeneration medium under light conditions. This regeneration medium permits the completion of embryo development. More than one regeneration medium can be used in succession or freshening of the same regeneration medium can be used to nurse embryo development.

6.3. DIFFERENTIATION

Asexual cacao embryos are transferred to differentiation medium in order to produce a shoot and root pole before germination is permitted. A series of successive transfers to different differentiation media (under dark or low light conditions) were used during this phase (see Tables I and II for the various culture media employed). Early and late differentiation subphases have been recognized during this phase as the embryos undergo transfer through the various differentiation media. During early differentiation, the embryos are allowed to complete the development up to torpedo shape and then a period of slow growth or arrested visual growth is provided through a late differentiation conditions. Higher ABA levels, high osmoticum and/or slow airdehydration on top of agar medium are preferably practiced during late differentiation to prepare the embryo for germination.

TABLE I

COMPOSITION OF CULTURE MEDIA USED FOR EARLY DIFFERENTIATION (SEVI A5) AND LATE DIFFERENTIATION (MLI) FOR CACAO SOMATIC EMBRYOS

| Compounds | SEVI A5 | MLI |
|---|---|---|
| Autoclaved: | | |
| Gamborg's B5 salts* | 0.25X | 0.25X |
| Inositol (mg/l) | 100.0 | 100.0 |
| Glycine | 50.0 | 50.0 |
| Cysteine (mg/l) | 60.0 | 60.0 |
| PBP-40 (g/l) | 3.0 | 3.0 |
| Malt extract (mg/l) | 25.0 | 25.0 |
| Sucrose (g/l) | 30.0 | 30.0 |
| Zeatin ($\mu$M) | 1.0 | — |
| GA$_3$ ($\mu$M) | 0.3 | — |
| ABA ($\mu$M) | 1.0 | 15.0 |
| GELRITE (g/l) | 2.4 | 2.4 |
| IAA ($\mu$M) | 0.5 | — |
| Filter Sterilized: | | |
| Kao's vitamins** | 10.0X | 10.0X |
| Final pH | 5.3 | 5.3 |

*Gamborg et al., 1968, Exp. Cell Res. 50: 151-158.
**Kao and Michayluk, 1975, Planta 126:105-110.

6.4 GERMINATION

Somatic embryos with a prominent shoot and root pole regions are transferred onto a germination medium (see Table II for germination media) to further develop primary leaves and roots. At completion of this step, young cacao plantlets are obtained.

TABLE II

| | CULTURE MEDIA COMOSITIONS FOR CACAO EMBRYOGENESIS | | | | | | | | |
|---|---|---|---|---|---|---|---|---|---|
| | REGENERATION MEDIA | | | DIFFERENTIATION MEDIA | | | GERMINATION MEDIA | | |
| Component | SEVIii | 4G | 4Gi/4 | 4P/13 | 4P/14 | 4P/14B | 4P/15 | 4P/16 | 15C/6 |
| Macroelements | 0.25X | 0.50X | 0.50X | 0.50X | 0.50X | 0.50X | 0.50X | 0.50X | 0.50X |
| Microelements | 0.25X | 0.0X | 1.0X | 1.0X | 0.50X | 0.50X | 0.50X | 0.50X | 0.50X |
| Iron Salt (MSV) | 0.25X | 1.0X | 1.0X | 1.0X | 1.0X | 1.0X | 1.0X | 1.0X | 1.0X |
| B5 Vitamins | 1.0X | 1.0X | 1.0X | 1.0X | 1.0X | 1.0X | 1.0X | 1.0X | 0.50X |
| Inositol (mg/l) | 100 | 100 | 100 | 100 | 100 | 100 | 100 | 100 | 0 |
| Vitamin B$_2$ (mg/l) | 0 | 0.1 | 0.05 | 0.1 | 0.1 | 0.1 | 0.1 | 0.1 | 0.1 |
| Cysteine (mg/l) | 200 | 200 | 200 | 200 | 200 | 200 | 200 | 0 | 0 |
| Glycine (mg/l) | 5 | 5 | 5 | 5 | 5 | 5 | 5 | 5 | 0 |
| Casine HCl (mg/l) | 0 | 0 | 0 | 500 | 500 | 500 | 100 | 100 | 0 |
| Malt Extract (mg/l) | 100 | 100 | 100 | 100 | 100 | 100 | 100 | 100 | 0 |
| CW (ml/l) | 50 | 50 | 50 | 0 | 0 | 0 | 25 | 25 | 25 |
| 6BA ($\mu$M) | 0 | 0 | 0 | 2.5 | 5.0 | 5.0 | 5 | 5 | 5 |
| ZEA ($\mu$M) | 1 | 2.5 | 2.5 | 2.5 | 2.0 | 2.0 | 2 | 2 | 0 |
| KIN ($\mu$M) | 0 | 0 | 1.5 | 0 | 0 | 0 | 0 | 0 | 0 |
| NAA ($\mu$M) | 0 | 1 | 0 | 1.5 | 1.5 | 1.5 | 1.5 | 0 | 0 |
| IAA ($\mu$M) | 0 | 0 | 0 | 0 | 0 | 0 | 0 | 1.0 | 1.0 |
| GA ($\mu$M) | 0.3 | 1 | 1 | 1.5 | 1.5 | 1.5 | 1.5 | 1.5 | 1.5 |
| ABA ($\mu$M) | 0.05 | 0.05 | 0.05 | 0.02 | 0.02 | 0.02 | 0.02 | 0.02 | 0.02 |
| PVP (g/l) | 5 | 5 | 5 | 5 | 5 | 5 | 5 | 5 | 0 |

TABLE II-continued

| | CULTURE MEDIA COMOSITIONS FOR CACAO EMBRYOGENESIS | | | | | | | | |
|---|---|---|---|---|---|---|---|---|---|
| | REGENERATION MEDIA | | | DIFFERENTIATION MEDIA | | | GERMINATION MEDIA | | |
| Component | SEVIii | 4G | 4Gi/4 | 4P/13 | 4P/14 | 4P/14B | 4P/15 | 4P/16 | 15C/6 |
| Charcoal (g/l) | | 0 | 0 | 0 | 2 | 5 | 2 | 5 | 5 |
| Sucrose (g/l) | 30 | 40 | 40 | 80 | 80 | 80 | 80 | 80 | 40 |
| Agar (g/l) | 9 | 9 | 9 | 8.5 | 8.0 | 8.0 | 8.0 | 8.0 | 8.0 |
| pH | 5.3 | 5.3 | 5.3 | 4.0 | 4.0 | 4.0 | 5.3 | 5.3 | 5.3 |
| Light Intensity | Low | Low | Low | Low | Low | Low | High | High | High |

6.5. PLANTLET DEVELOPMENT

All culture Phases 1–4 are conducted on solidified agar or GELRITE medium. At this step, cacao plantlets are removed from the solid medium, washed in sterile water, treated with a powder of rooting hormones (IAA or NAA 200–600 ppm or a mixture of both), and inoculated in sterile soil mix containing half strength MS salts and zeatin (0.5–2 $\mu$M) to generate mature plantlets.

6.6 HARDENING IN A GREENHOUSE

Mature plantlets with 2–4 flushes of primary leaves and an acceptable root system (primary and secondary roots) are transferred from laboratory growth chambers to shaded areas of a greenhouse (20% sunlight). Before moving these mature cacao plantlets from the laboratory to the greenhouse, they are immersed in a fungicide solution and then transferred to small pots (3-inch size) or growing cones (10 cu inches) containing the same soil mix and nutrients described in Section 6.5., supra. Each mature plantlet is covered with a PVC film to protect against excess dehydration. During the first 1–2 weeks, small holes are made in these PVC covers and later these PVC film are removed completely. The mature cacao plantlets from somatic embryos are kept under a special section of the greenhouse with a fog system until they are transferred to one-five gallon pots where they grow into mature plants.

Data with respect to the number of mature plants recovered from non-zygotic explants and efficiencies of recovery for each phase are given in Table III, infra. The calculation of the efficiency of each phase is based on the ratio between the number of units recovered divided by the total number of units inoculated or cultured.

TABLE III

RECOVERY OF CACAO PLANTS USING THE SOMATIC EMBRYOGENESIS PROCESS OF SECTION 6

| CULTURE PHASE | NUMBER OF CULTURES | EFFICIENCY RATE/PHASE (%) |
|---|---|---|
| Primary explants | 30,160 | |
| Primary embryos | 948 | 3.0 |
| Secondary explants* | 88,134 | |
| Regenerated embryos | 35,525 | 40.3 |
| Embryos in differentiation | 35,525 | |
| Differentiated embryos | 6,174 | 17.4 |
| Embryos in germination | 6,174 | |
| Germinated embryos | 569 | 9.2 |
| Plantlets germinated | 569 | |
| Mature Plantlets | 136 | 23.9 |
| Mature Plantlets at hardening | 16 | |
| Hardened mature plantlets | 38 | 27.9 |
| Mature Plants in soil | 8 | 21.1 |

*Secondary explants are obtained from in vitro embryos which were obtained from primary embryos as well as tissue from embroyonic tissue.

7. EXAMPLE 2: PROTOCOL FOR SOMATIC EMBRYOGENESIS FROM IMMATURE PETAL TISSUES

Young flower buds are exercised from adult cacao plants and surface sterilized in 0.8% sodium hypochlorite for 10 minutes. Young flower bud petals are isolated with dissecting needles under a stereoscope using sterile glass slides. Immediately after isolation, all young petals are transferred onto the following primary culture medium: full strength MS inorganic salts, inositol (550 $\mu$M), thiamine (30 $\mu$M), pyridoxine (15 $\mu$M), nicotinic acid (15 $\mu$M), 2,4-D (10 $\mu$M), kinetic (1 $\mu$M), sucrose (40 g/l), pH 5.5, autoclaved. Alternatively, the following primary culture medium can be used: half strength MS salts, thiamine (30 $\mu$M), pyridoxine (15 $\mu$M), nicotinic acid (15 $\mu$M), inositol (550 $\mu$M), casein HCl (500 mg/l), glycine (5 mg/l), cysteine (250 mg/l), PVP (5 g/l), malt extract (500 mg/l), sucrose (60 g/l), coconut water (100 m/1), 2,4-D (15 mg/l), 2-iP (2.5 $\mu$M), pH 5.3, autoclaved. Petals from 6 mm long flower buds exhibit the best response; however, buds of from about 4 mm to about 8 mm can be employed. A pretreatment at 10° C. for 24 hours before inoculation onto the primary culture medium is beneficial for regeneration The cultures are maintained at 23°–25° C. under dark conditions.

After 3 weeks on primary culture medium, direct embryogenesis is observed on the basal portion of young petal explants. Callus formation is observed on the distal end of young petals. Tissues containing the early stage of somatic embryos (globular to heart shape) are transferred to the following regeneration liquid medium: MS salts, coconut water (100 ml/l), sucrose (50 g/l), pH 5.3. Different genotypes have been noted to vary in their capacity to regenerate under these conditions. Adjustments to the medium may be necessary to provide optimal regeneration depending on the genotype cultured.

Once the young somatic embryos derived from immature petals are removed from the original tissues, they are cultivated in culture media already described for nucellus-derived embryos, i.e. media of Sections 6.1.–6.6., supra. The culture conditions and physical parameters are the same as the ones used for nucellus embryos.

Data with respect to the number of mature plants recovered from non-zygotic explants and efficiencies of recovery for each phase are given in Table IV, infra. The calculation of the efficiency of each phase is based on the ratio between the number of units recovered divided by the total number of units inoculated or cultured.

TABLE IV

RECOVERY OF CACAO PLANTS USING THE SOMATIC EMBRYOGENESIS PROCESS OF SECTION 7

| CULTURE PHASE | NUMBER OF CULTURES | EFFICIENCY RATE/PHASE (%) |
|---|---|---|
| Primary explants | 27,721 | |
| Primary embryos | 167 | 0.1 |

TABLE IV-continued
RECOVERY OF CACAO PLANTS USING THE SOMATIC EMBRYOGENESIS PROCESS OF SECTION 7

| CULTURE PHASE | NUMBER OF CULTURES | EFFICIENCY RATE/PHASE (%) |
| --- | --- | --- |
| Secondary explants* | 75,954 | |
| Isolated embryos | 26,961 | 35.5 |
| Embryos in differentiation | 26,961 | |
| Differentiated embryos | 22,819 | 84.6 |
| Embryos in germination | 4,116 | |
| Germinated embryos | 880 | 21.4 |
| Plantlets germinated | 880 | |
| Mature plantlets | 155 | 17.6 |
| Mature plantlets at hardening | 155 | |
| Hardened mature plantlets | 32 | 20.6 |
| Mature plants in soil | 7 | 21.8 |

*Secondary explants are obtained from in vitro embryos which were obtained from primary embryos as well as tissue from embryonic tissue.

8. EXAMPLE 3: MICROPROPAGATION OF CACAO SOMATIC EMBRYOS USING GRAFTING TECHNIQUES

An alternative way of utilizing cacao somatic embryos in a micropropagation scheme is to use grafting techniques. In this case, cacao somatic embryos derived from either nucellus or young petal tissues have been utilized since they represent the true type of the donor cacao plant. The scion was nucellus- or petal-derived somatic embryos from the differentiation phase, measuring about 0.5-1.5 cm long. The root stock was 4-week-old cacao seedlings treated with a side incision at 2.0 cm above the cotyledonary node. Somatic embryos were soaked in a solution containing 10% coconut water and 0.3 g/l Manzate. A lateral cut was made on each somatic embryo at the base of the hypocotyl (root pole) and immediately placed on the cut surface of the root stock. The graftings were held by a parafilm strip, covered with a PVC bag and kept under a mist chamber at 80% shading. After 6-8 weeks, visible shoot growth of the scions was observed; these scions then grew into mature cacao plants under normal greenhouse conditions. Several other grafting techniques have also been practiced with cacao somatic embryos, i.e., top cut above cotyledonary node, the same with a central incision (cleft type), and lateral incision below the cotyledonary node. However, the preferred method is the grafting technique described above. Axillary shoots from the cotyledonary node were observed, but they were removed on a regular basis to avoid competition with the grafted scion.

9. EXAMPLE 4: PROCEDURE OF CACAO MICROPROPAGATION BY SOMATIC EMBRYOGENESIS OF NUCELLUS AND PETAL EXPLANTS

9.1. INDUCTION PHASE

Nucellus and petal explants are used for induction of cacao somatic embryogenesis. Both tissues are isolated from mature trees and are non-zygotic in origin. A flow diagram for the micropropagation of cacao via somatic embryogenesis with an average time line is given in FIG. 1.

9.1.1. NUCELLUS EXPLANTS

Nucellus explants are derived from immature seeds excised from young fruits. A schematic representation is shown in FIG. 2. 1 shows young fruit before cutting, measuring 5-12 cm long, 2.5-3.5 cm in diameter. 2 shows that both ends of the young fruit must be cut. 3 shows that the fruit is sectioned into four quarters. 4 shows an immature seed cavity. 5 shows a seed coat. 6 shows nucellus tissue just inside the seed coat. 7 shows a cavity containing the liquid endosperm. 8 shows nucellus explant isolated from the seed coat. 9 shows the lower extremity of the nucellus tissue which is cut off to eliminate the zygotic embryo. Photographs of the above-mentioned steps are shown in FIG. 5.

It is advantageous that the size of young cacao fruits be selected prior to isolation of nucellus explants. The size of selected fruit ranges from 5-12 cm in length and from 2.5-3.5 cm in width depending on the genotype (see FIG. 5A). The best size of immature fruits for most genotypes has been about 7-9 cm in length. Such fruits still contain a liquid endosperm and a layer of nucellus (ca. 2 mm of thickness). As the fruit matures, the nucellus layer surrounding the embryo thins out. On the other hand, if the fruit is too young, it is difficult to separate the nucellus layer from other tissues in the immature seeds. Also the ability of the nucellus to proliferate in vitro and to regenerate will be affected by the age of the fruit, genotype and physiological condition of the donor plants. An apparent increased rate of success is found with fruits collected during the active growing season, typically, November-April in Belize.

Cacao fruits are surface sterilized with 20% Clorox for 30 min. followed by three rinses in sterile water. After cutting off the two ends of each fruit (see FIG. 5B), four sections are made lengthwise on sterile filter paper (see FIG. 5C). Preferably, each immature seed is cut into two halves with the zygotic embryo in the basipetal end of the seed (see FIG. 5D). Nucellus tissue is carefully separated from the seed coat. The portion of the immature seed containing the zygotic embryo is preferentially discarded. Twenty nucellar explants (see FIG. 5E) are cultured on 100×10 mm Petri dishes charged with primary culture medium CA-200 (Table V) sealed with PVC film, and incubated in the dark at 26°±2° C. The most important components of CA-200 are 2,4-D, coconut water and Kao's vitamins. Primary embryos appear 4 weeks after inoculation. If there are any zygotic embryos inoculated due to abnormal positioning in the young fruit, they will develop and grow immediately and they will be detected within the first 10-15 days in the primary culture phase. Developed zygotic embryos can be easily recognized by their size and the presence of single embryos not associated with underlying callus tissues. They can be eliminated before the somatic embryos (SE) are fully developed.

TABLE V
PRIMARY CULTURE MEDIUM FOR CACAO NUCELLUS CULTURE (CA-200)

| Compounds | Final Concentration |
| --- | --- |
| Kao's salts* | 1.0X |
| Sucrose | 20,000 mg/l |
| Glucose | 20,000 mg/l |
| PVP-40 | 5,000 mg/l |
| GELRITE (Kelco) | 2,400 mg/l |
| Coconut Water | 50 ml/l |
| pH | 5.6 |
| (Autoclave 17 mins., 250° F.) | |
| Kao's Vitamins* | 1.0X |
| Kao's Organic acids* | 1.0X |
| Kao's Amino acids* | 1.0X |
| Kao's sugars & sugar alcohols* | 1.0X |

TABLE V-continued

PRIMARY CULTURE MEDIUM FOR CACAO NUCELLUS CULTURE (CA-200)

| Compounds | Final Concentration |
| --- | --- |
| MES | 600 mg/l |
| 2,4-D | 3.0 μM |
| pH | 5.6 |
| (Filter sterilized above) | |
| After combining the above two portions pour into 100 × 10 mm plates (25 ml/plate) | |

*Kao and Michayluk, 1975, Planta (Berl.) 126: 105-110

The somatic embryogenic process from nucellus explants can take place through a direct or indirect pathway. Indirect embryogenesis is characterized by the proliferation of embryogenic tissue while still on medium CA-200. The embryogenic tissue will continue to produce primary embryos for several months without subculture.

9.1.2. PETAL EXPLANTS

Immature flower buds, in which the sepals are unopened, are used for culturing cacao petals. A schematic representation is shown in FIG. 3. 1 shows intact young flower bud with pale green color measuring 3-5 mm in length. 2 shows the relative position of the cutting line made to excise the petal explants. 3 shows the isolated petal explant before setting in culture. There are five young petals per flower bud. 4 shows an illustration of the presence of five sepals. 5 shows an illustration of the five anthers and respective filaments. 6 shows an illustration of the ovary. 7 shows Staminodes (total of five). 8 shows a remaining portion of the flower bud after cutting. Photographs of the abovementioned steps are shown in FIG. 6.

The best size for the young flower buds is 3-5 mm in length depending on the genotype and growing conditions (see FIG. 6A). After surface sterilization with 10-15% Clorox for 15 minutes followed by three rinses with sterile water, the flower base where the petals connect with the flower is cut off to free the petals (see FIG. 6B). The anthers and filaments will remain attached to the ovary if the cut flower base portion is not longer than 1/10 to ¼ of the total length of the flower bud. In this way, the petals are easily removed and the anthers are eliminated.

Young petals are cultured on the primary culture medium CRVI/2 (Table VI) for 4 weeks in the dark at 26°±2° C. Twenty explants are inoculated in 100×10 mm petri dishes. Callus tissues are transferred to the medium CRVI/2-2 (Table VII) for several months in the dark and monthly evaluations are made to isolate somatic embryos.

TABLE VI

MEDIUM FOR CACAO PETALS, PRIMARY CULTURE (CRVI/2)

| Compounds | Final Concentration |
| --- | --- |
| MS Salts* | 1.0X |
| Coffee Vitamins** | 1.0X |
| Inositol | 100 mg/l |
| Sucrose | 40,000 mg/l |
| GELRITE (Kelco) | 2,400 mg/l |
| 2,4-D | 10.0 μM |
| Kinetin | 1.0 μM |
| (Autoclave for 17 min., 250° F.; Pour into 100 × 10 mm plates (25 ml/plate) | |

*Murashige and Skoog, 1962, Physiol. Plant. 15:473-497.
**Sondahl and Sharp, 1977, Z. Pflanzen Physiol. 81:395-408.

TABLE VII

MEDIUM FOR CACAO PETALS, SECONDARY CULTURE (CRVI/2-2)

| Compounds | Final Concentration |
| --- | --- |
| MS Salts* | 0.5X |
| Coffee Vitamins** | 1.0X |
| Inositol | 100 mg/l |
| Sucrose | 40,000 mg/l |
| Charcoal (Sigma 100-400 mesh) | 2,000 mg/l |
| GELRITE (Kelco) | 2,400 mg/l |
| 6-BA | 5.0 μM |
| Initial pH | 3.5 (before autoclaving) |
| Final pH | 5.3 |
| (Autoclave for 17 min., 250° F.) | |
| Pour into 100 × 10 mm plates (25 ml) | |

*Murashige and Skoog, 1962, Physiol. Plant. 15:473-497.
**Sondahl and Sharp, 1977, Z. Pflanzen Physiol. 81:395-408.

9.2 REGENERATION PHASE

Somatic embryos from both nucellus and petal explants can be derived from two distinct pathways, direct and indirect somatic embryogenesis. When primary embryos are well developed, as shown by the presence of cotyledons and a hypocotyl length of approximately 2-7 mm, they are transferred onto differentiation medium (see Tables IX-X). Alternatively, primary embryos including cotyledons and hypocotyls are used as an explant source for secondary embryo production on regeneration medium (see Table VIII, MSE-VIK medium). After a period of 4 weeks on regeneration medium the young embryos and embryogenic tissues are transferred to fresh regeneration medium. Whenever the size of somatic embryos permit, the young embryos are cut into segments of 3-5 mm in size to further increase secondary embryo production while incubated in MSE-VIK medium. If the size of the embryos are still smaller than 6 mm, they are transferred as is to fresh MSE-VIK medium. This subculture process is repeated every 3-4 weeks, and serves to amplify the original number of cacao embryos of non-sexual origin. Numerous secondary embryos are regenerated from this medium, most of them are in clusters.

Schematic representations of normal and abnormal embryos in various stages of development are shown in FIG. 4. A shows the late globular or heart shape stage. B shows the early torpedo stage embryo before cotyledon development. C shows the late torpedo stage embryo with developing cotyledons. D shows a somatic embryo with the presence of large cotyledons. E shows elongated somatic embryo without cotyledons. F shows young somatic embryo with secondary embryo differentiation. G shows torpedo stage embryos with proliferation of embryogenic tissue from cotyledonary leaves. H shows abnormal embryo with aborted hypocotyl and oversize cotyledons. I shows very large globular structure that does not follow normal embryo development. Preferentially, ivory colored, normal-shaped embryos are transferred to the differentiation phase. Photographs of normal and abnormal embryos are shown in FIG. 8. Photographs of the above-mentioned procedure are shown in FIG. 9. This subculture process in regeneration medium is repeated many times in order to produce the desirable number of secondary embryos. These embryos are then the major source of cacao somatic embryos for micropropagation purposes. All explants for secondary embryo production are inoculated in 100×10 mm Petri dishes containing 20 explants per dish and cultivated in the dark at 26°±2° C.

TABLE VIII

MEDIUM FOR CACAO EMBRYO REGENERATION (MSE-VIK)

| Compounds | Final Concentration |
|---|---|
| MS Salts* | 0.25X |
| Inositol | 100 mg/l |
| Cysteine | 200 mg/l |
| Malt extract (Sigma) | 50 mg/l |
| PVP-40 | 5,000 mg/l |
| sucrose | 30,000 mg/l |
| GELRITE (Scott) | 2,400 mg/l |
| Glycine | 3.75 mg/l |
| Zeatin | 1.0 μM |
| Coconut water | 50.0 ml/l |
| pH | 5.3 |
| (Autoclave above for 17 min., 250° F.) | |
| Kao's vitamins** | 1.0X |
| After combining the above two portions pour in 100 × 10 mm plates (25 ml/plate). | |

*Murashige and Skoog, 1962, Physiol. Plant. 15:473–497.
**Kao and Michayluk, 1975, Planta (Berl.) 126:105–110.

For effective production of somatic embryos, great attention must be paid to the quality of embryogenic tissues. The friable embryogenic tissue containing very small globular clusters of ivory colored embryos are the most effective tissue for achieving differentiation. This friable embryogenic tissue should be carefully distinguished from other callus types like the soft callus or yellow hard callus or white callus which do not have regeneration capacity. Direct somatic embryogenesis is also observed on MSE-VIK. In this case, the embryos arise directly from the explant segments.

Translucent globular embryos generally do not proceed on a normal developmental pattern. Reversion of translucent to the ivory embryo type may occur during the beginning of the embryo differentiation process. Partially oxidized embryogenic tissues also can be subcultured since additional embryos are recovered from them. A strict subculture regimen of 3–4 week intervals is the best mechanism for maintaining the viability of the embryogenic tissue and for assuring a high frequency of embryo regeneration.

9.3. DIFFERENTIATION PHASE

The differentiation phase consists of two subphases: (a) early differentiation and (b) late differentiation (see FIG. 9). All embryos in the differentiation phase are cultivated in 100×10 mm Petri dishes, 20 embryos per dish and incubated in the darkness at 26°±2° C. A range of differentiation media containing ABA (100–200 μM) and with or without 6-BA (50 μM) have been used with success. One such medium used is EM-3 (Table IX). A second differentiation medium (MMO medium; Table X) is used in the late differentiation phase.

Single ivory embryos at the late globular or heart shape stage (FIG. 9A) to early torpedo shape (FIG. 9B) are transferred onto the early differentiation medium. There is a preference to transfer from regeneration to differentiation media embryos in the size range of 2–7 mm in length.

After 4 weeks of culture on early differentiation medium (see EM-3, Table IX), embryos that reach 6–10 mm and possess a normal shape and no oxidation can be transferred onto late differentiation medium (see Table X, MMO medium) for an additional 8 weeks. Abnormally-shaped embryos, oxidized or translucent embryos are discarded and not transferred to the next culture phase.

TABLE IX

MEDIUM FOR CACAO EARLY DIFFERENTIATION (EM-3)

| Compounds | Final Concentration |
|---|---|
| MS macro salts* | 0.5X |
| MS micro salts* | 0.5X |
| MS Iron* | 0.5X |
| MgSO$_4$.7H$_2$O | 74 mg/l |
| Inositol | 100 mg/l |
| Glycine | 3.75 mg/l |
| Cysteine | 200 mg/l |
| Malt extract (Sigma) | 100 mg/l |
| Casein HCl | 250 mg/l |
| PVP-40 | 5,000 mg/l |
| Sucrose | 80,000 mg/l |
| GELRITE (Scott) | 2,400 mg/l |
| Charcoal (Sigma 100–400 mesh) | 3,000 mg/l |
| 6-BA | 50 μM |
| ABA | 150 μM |
| Initial pH | 4.9 (before autoclaving) |
| Final pH | 5.5 |
| (Autoclave above for 17 min., 250° F.) | |
| Coffee vitamins** | 1.0X |
| Kao'vitamins*** | 1.0X |
| (Filter sterilize above three) | |

*Murashige and Skoog, 1962, Physiol. Plant. 15:473–497.
**Sondahl and Sharp, 1977, Z. Pflanzen Physiol. 81:395–408.
***Kao and Michayluk, 1975, Planta (Berl.) 126:105–110.

TABLE X

MEDIUM FOR CACAO LATE DIFFERENTIATION (MMO)

| Compounds | Final Concentration |
|---|---|
| MS salts* | 0.25X |
| MS Iron* | 1.0X |
| PVP-40 | 5,000 mg/l |
| Sucrose | 5,000 mg/l |
| Sorbitol | 40,000 mg/l |
| Inositol | 39,600 mg/l |
| Agar purified (Sigma) | 6,500 mg/l |
| MES | 1,000 mg/l |
| pH | 5.5 |
| (Autoclave above for 17 min., 250° F.) | |
| Cysteine | 200 |
| Kao'vitamins** | 10.0X |
| Kao's sugars & sugar alcohol** | 1.0X |
| Asparagine | 10.0 mg/l |
| Arginine | 10.0 mg/l |
| Glutamine | 10.0 mg/l |
| ABA | 1.0 μM |
| pH = 5.5 | |
| (Filter sterilize above) | |

*Murashige and Skoog, 1962, Physiol. Plant. 15:473–497.
**Kao and Michayluk, 1975, Planta (Berl.) 126:105–110.

9.4 GERMINATION PHASE

Specific criteria can be used to select and advance mature SEs to the germination phase.

a) Size: Somatic embryos are preferably longer than 10 mm since smaller SEs do not germinate very well.

b) Viability: Viable SEs are essential for germination. Preferably, the oxidation degree should be lower than grade 3 (ca. 50% oxidation) using a scale of 1–5 whereby #1 is normal and #5 is highly oxidized. Once again, ivory or cream-colored embryos perform best during germination.

c) Shape: The somatic embryos with a straight or slightly curved hypocotyl, with or without developed cotyledons are used. Embryos with defects (accentuated curves, oxidized, etc.) are discarded. Abnormal somatic embryos with coiled hypocotyls, embryos with very large cotyledons, or embryos with very small aborted-like hypocotyls are discarded. Somatic embryos with well developed shoot tips are considered the best quality for germination. However, experience has shown that somatic embryos without visible shoot tips, protuberances, or large elongated epicotyls can still germinate.

The embryos germinate better if they are first cultivated in a liquid germination medium (G-26/6, Table XI). Three to five embryos are placed in Erlenmeyer flasks (125 ml size) charged with 10 ml of medium and incubated on an orbital shaker at 100 rpm for 5-10 days. The liquid medium allows for efficient embryo nutrition and also allows for leaching of deleterious metabolites that may be present in the embryo tissue.

TABLE XI

LIQUID MEDIUM FOR CACAO GERMINATION (G26/6)

| Compounds | Final Concentration |
|---|---|
| WPM Salts* | 1.0X (K$_2$SO$_4$ 0.5X) |
| KNO$_3$ | 400 mg/l |
| Inositol | 100 mg/l |
| Coconut Water | 100 ml/l |
| Casein HCl | 750 mg/l |
| Cysteine | 200 mg/l |
| Malt extract (Sigma) | 50 mg/l |
| Sucrose | 40 g/l |
| NAA | 1.0 µM |
| GA | 3.0 µM |
| Glycine | 50 µM |
| Coffee vitamins** | 1.0X |
| Charcoal (Sigma, C-3790) | 0.5 g/l |
| (Autoclave for 17 min, 250° F.) | |
| pH | 5.5 (final) |
| | 5.3 (before autoclave) |
| 10 ml in each 125 ml flask shake at 100 rpm | |

*Lloyd and McCown, 1981, Int. Plant Prog. Soc. Proc. 30:421-427.
**Sondahl and Sharp, 1977, Z. Pflanzen Physiol. 81:395-408.

The shallow liquid germination medium on shakers provides very good aeration and nutrient condition. The flasks are kept in a lighted room (Grow Lux lamps with ca. 1,000 lux) with a temperature cycle of 30° C. in light for 10 hrs. and 22° C. in the dark for 14 hrs. After implanting green primary leaves and expanded cotyledons that are capable of photosynthesis, the SEs are transferred to a solid germination medium WPM-5A (Table XII) in an erect position. Culture jars (4 oz.) are charged with 50 ml of WPM-5A and sealed with transparent film (SUNCAP; Sigma). Two embryos are placed in each jar. At his stage, the culture jars are transferred to growth chambers with or without high $CO_2$ and high light intensity to stimulate shoot tip development. Specifically, fluorescent and Grow lux types of lights are used and a total of 7,000-10,000 lux (ca. 175-250 µE·m$^{-2}$·s$^{-1}$) is desirable. Photographs of germinated embryos are shown in FIG. 10A.

TABLE XII

SOLID MEDIUM FOR CACAO GERMINATION (WPM-5A)

| Compounds | Final Concentration |
|---|---|
| WPM Salts* | 1.0X |
| Inositol | 100 mg/l |
| Fructose | 15 g/l |
| Coffee Vitamins** | 0.5X |
| 6-BA | 5 µM |
| IAA | 0.5 µM |
| Glycine | 50 µM |
| Charcoal (Sigma, C-3790) | 5 g/l |
| GELRITE | 3.5 g/l |
| pH | 5.4 |
| (pH equal to 3.5 before adding charcoal and autoclaving) | |
| Pour in 4 oz. glass jars (50 ml/jar) and autoclave for 17 | |

TABLE XII-continued

SOLID MEDIUM FOR CACAO GERMINATION (WPM-5A)

| Compounds | Final Concentration |
|---|---|
| min., 250° F. | |

*Lloyd and McCown, 1981, Int. Plant Prog. Soc. Proc. 30:421-427.
**Sondahl and Sharp, 1977, Z. Pflanzen Physiol. 81:395-408.

9.5. PLANTLET DEVELOPMENT PHASE

Only plantlets that develop in germination medium to the point of producing at least one true leaf with normal green color and obtain a hypocotyl length of at least 10 mm are selected to be transferred to the growth and development phase. In general, the presence of two or more leaves is more desirable to transfer to this phase.

The development of roots during the germination phase has not been considered critical for transferring to the Growth Phase. A well developed shoot system will promote root growth in a short period of time after being transferred to the growth phase.

Plantlets from the germination phase with the above characteristics are transferred onto fresh medium WPM-5A (Table XII), incubated in a growth chamber with or without $CO_2$ enrichment (1,000-2,000 ppm) and high light intensity (7,000-10,000 lux). The physical conditions of the growth chamber are adjusted to a temperature cycle of 30° C. -22° C. day/night and a photoperiod of 10/14 h day/nigh cycle. Alternatively, the plantlets can be kept in the same solid germination medium (WPM-5A, Table XII) for an extended period of time to allow further vegetative growth. A photograph of the mature plantlet is shown in FIG. 10B. When this procedure is adopted, a liquid film of WPM-5B (Table XIII) is added on the surface of the solid germination medium (WPM-5A, Table XII) to supplement the mature plantlets with fresh nutrients and avoid excessive desiccation of the solid medium. Weekly aliquots of 2-4 ml of liquid WPM-5B are added to each 4-8 oz. jars, respectively. To avoid excessive salt build up, further dilution of WPM-5B or even sterile water can be used as liquid film during this plantlet development phase. The liquid film provides moisture to the solid medium allowing flow of the nutrients to the young plantlets.

TABLE XIII

LIQUID MEDIUM FOR CACAO MATURE PLANTLET DEVELOPMENT (WPM-5B)

| Compounds | Final Concentration |
|---|---|
| WPM salts* | 0.5X |
| Inositol | 100 mg/l |
| Fructose | 15 g/l |
| Coffee vitamins** | 0.5X |
| 6-BA | 5 µM |
| IAA | 0.5 µM |
| Glycine | 50 µM |
| pH | 5.4 |
| (Autoclave 17 min., 250° F. Used as a liquid medium adding on the surface of the solid medium, WPM-5 (Table XII) | |

*Lloyd and McCown, 1981, Int. Plant Prog. Soc. Proc. 30:421-427.
**Sondahl and Sharp, 1977, Z. Pflanzen Physiol. 81:395-408.

9.6. HARDENING PHASE

After attaining acceptable shoot growth (more than 4-5 true leaves) and further development of the root system, the mature plantlets are transferred into pots filled with an artificial soil mixture, Metro-Mix 200 with 50% sand (grade #1) (Table XIV), and covered with plastic bags. Mature plantlets will still remain in the growth chamber for approximately 25 days and the soil is kept moist at all times with 0.1X R-15 solution (Table XV). During this period, a progressive number of holes are made with a sharp pencil on the plastic bag for better hardening-off.

The pots are finally transferred to a greenhouse section equipped with 80% shading and a regular fog system activated at 15 min. intervals. The hardened mature plantlets continue to receive routine care, including periodic nutrient R-15 solution. After 2-3 weeks, the mature plants are removed from the fog bench and transferred to standard greenhouse conditions. A photograph of such plants are shown in FIG. 10C. A photograph of cacao fruits and flower buds on such plants is shown in FIG. 10F.

TABLE XIV
MEDIUM FOR HARDENING-OFF CACAO PLANTLETS (R-15*)

| Stock Solution Number | Compound | Final Concentration | (mg/l) | Stock Solution (g/l) | Stock Solution Volume* (ml) |
|---|---|---|---|---|---|
| Macronutrients | | (mM) | | | |
| I | $KNO_3$ | 12 | 1,200 | 101.1 | 12 |
| II | $Ca(NO_3)O_2.4H_2O$ | 4 | 945 | 236.16 | 4 |
| III | $NH_4H_2PO_4$ | 2 | 231.6 | 115.08 | 2 |
| IV | $MgSO_4.7H_2O$ | 2 | 493 | 246.49 | 2 |
| Micronutrients | | ($\mu$M) | | | |
| V | $FeSO_4.7H_2O$ | 0.4 | 0.11 | 37.3 | 4 |
| | $Na_2EDTA$ | 0.5 | 0.15 | 27.8 | 4 |
| VI | $H_3BO_3$ | 12.5 | 0.773 | 1.55 | |
| | $MnSO_4H_2O$ | 1.0 | 0.169 | 0.34 | |
| | $ZnSO_4.7H_2O$ | 1.0 | 0.288 | 0.58 | 1 |
| | $CuSO_4.5H_2O$ | 0.5 | 0.0625 | 0.13 | |
| | $(NH_4)_6.MO_7O_{24}.4H_2O$ | 0.5 | 0.309 | 0.62 | |
| | pH = 5.4 | | | | |

*Based on a modified Hoagland solution after Johanson, C. M., Stout, P. R., Broyer, T. C. and Calton, A. B. (1957): Comparative chlorine requirements of different plant species. Plant and Soil 8:337-353.

TABLE XV
SUBSTRATE USED FOR MATURE COCAO PLANTLET DEVELOPMENT (PD-04)

| Substrate | Metro-Mix 200* plus pure sand, grade #1, (1:1) |
|---|---|
| Solution for moistening the substrate | 0.1X R15 liquid** |
| Pots used for the plantlets | 4 in (square) 3 in. (round) |
| | (Substrates not sterilized) |

*E. C. Geiger Co., Harleysville, PA
**See Table XIV

Data with respect to the number of plants recovered from various cacao clones are shown in Table XVI, infra. Data with respect to the number of mature plants recovered from non-zygotic explants and efficients of recovery from each phase are given in Table IV, infra. The calculation of efficiency of each phase is based on the ratio between the number of units recovered divided by the total number of units inoculated or cultured.

TABLE XVI
RECOVERY OF CACAO PLANTS USING THE SOMATIC EMBRYOGENESIS PROCESS OF SECTION 9

| CULTURE PHASE | NUMBER OF CULTURES | EFFICIENCY RATE (%) |
|---|---|---|
| Primary explants | 5,623 | |
| Primary embryos | 3 | 0.1% |
| Secondary explants* | 52,934 | |
| Secondary embryos | 24,684 | 46.6% |
| Embryos in | 24,684 | |
| differentiation | | |
| Mature embryos | 20,921 | 84.8% |
| Embryos in germination | 2,250 | |
| Germinated embryos | 691 | 30.7% |
| Plantlets Germinated | 691 | |
| Developed plantlets | 202 | 29.3% |
| Mature plantlets at hardening | 202 | |
| Hardened mature plantlets | 50 | 24.8% |
| Mature plants in soil | 24 | 48.0% |

*Secondary explants are obtained from in vitro embryos which were obtained from primary embryos as well as tissue from embryonic tissue.

10. EXAMPLE 5: SOMATIC EMBRYOGENESIS OF CACAO THROUGH CELL SUSPENSION (PROTOCOL I)

A coarse type of cell suspensions were established from fresh isolated cacao friable embryogenic tissue. High frequency of embryo regeneration was achieved upon transferring liquid cultures to a solid regeneration medium.

10.1. MATERIALS AND METHODS

To induce the friable embryogenic tissue (FET), in vitro cotyledons of somatic embryos cultured on solid medium were used as source of explants. All cultures refer to the cacao genotype UF-667 (International Cacao Cultivar Catalogue, Technical Series, Technical Bulletin No. 6, Jorge Soria V. and Gustavo A. Enriquez, eds., Tropical Agricultural Research and Training Center, Turrialba, Costa Rica, 1981).

The explants were cut into pieces of 0.5-1.0 cm² and inoculated onto a solid primary culture primary culture medium (Multi-V) and incubated in dark conditions (27°-30° C.) for 4-6 weeks. The Multi V solid medium contained 0.25 X MS salts and organic compounds supplemented with 1-3 $\mu$M 2-iP or 0.5-4 $\mu$M 6-BA (experiment I). In experiment II, other plant growth regulator treatments were studied: 3-15 $\mu$M 2-iP with or without 1-5 $\mu$M 2,4-D were also tested (see Tables XVII-XIX).

In order to initiate a coarse embryogenic suspension, ca. 1 gram f.w. of friable embryo tissue (FIG. 11A) was inoculated into 20 ml CCS liquid medium (Table XX) in 125 ml flasks, shake on an orbital shaker at 160 rpm in darkness. The volume of the suspension was increased to 35 ml in darkness. These coarse cacao suspension cultures were allowed to multiply for more than 3 months. Subcultures are made every 7-10 days by replacing ⅓-½ volume with fresh medium.

TABLE XVII

BASIC MEDIUM FOR INDUCTION OF EMBRYOGENIC TISSUE FROM CACAO COTYLEDONARY EXPLANTS ON SOLID MULTI-V MEDIUM[1]

| Compounds | Concentration |
|---|---|
| MS Salts | 0.25X |
| Inositol | 100 mg/l |
| Glycine | 50 μM |
| Cysteine | 200 mg/l |
| Malt Extract | 50 mg/l |
| PBP-40 | 5 g/l |
| Sucrose | 30 g/l |
| GELRITE | 2.4 g/l |
| Kao's Vitamins | 1.0X |
| pH | 5.3 |
| 2-iP | 3.0 μM |

[1]Embryo regeneration medium has the same composition as above without 2-iP and the addition of NAA (4.0 μM).

TABLE XVIII

INDUCTION EFFICIENCY OF CACAO EMBRYOGENIC TISSUE ON MULTI-V MEDIUM (EXPERIMENT I)

| Exp. No. | Number of Explants | Growth Regulator | Conc. (μM) | No. explants with embryogenic tissue | Efficiency (%) |
|---|---|---|---|---|---|
| 1 | 108 | 6-BA | 0.5 | 20 | 18.5 |
| 2 | 108 | 6-BA | 1.0 | 21 | 19.4 |
| 3 | 96 | 6-BA | 1.5 | 24 | 25.0 |
| 4 | 96 | 6-BA | 2.0 | 17 | 17.7 |
| 5 | 108 | 6-BA | 3.0 | 25 | 23.1 |
| 6 | 108 | 6-BA | 4.0 | 19 | 17.6 |
| 7 | 108 | 2-iP | 1.0 | 24 | 22.2 |
| 8 | 96 | 2-iP | 1.5 | 23 | 23.9 |
| 9 | 108 | 2-iP | 2.0 | 23 | 21.3 |
| 10 | 96 | 2-iP | 3.0 | 30 | 31.3 |

TABLE XIX

INDUCTION EFFICIENCY OF CACAO EMBRYOGENIC TISSUE ON MULTI-V MEDIUM (EXPERIMENT II)

| Exp. No. | Number of Explants | 2-iP (μM) | NAA (μM) | 2,4-D (μM) | No. of explant with embryogenic tissue | Efficiency (%) |
|---|---|---|---|---|---|---|
| 1 | 60 | 3.0 | | | 37 | 61.7 |
| 2 | 40 | 4.0 | | | 19 | 47.5 |
| 3 | 60 | 4.0 | | | 24 | 10.0 |
| 4 | 60 | 10.0 | | | 27 | 45.0 |
| 5 | 60 | 15.0 | | | 12 | 20.0 |
| 6 | 60 | 3.0 | 1.0 | | 21 | 35.0 |
| 7 | 60 | 3.0 | 3.0 | | 18 | 30.0 |
| 8 | 60 | 3.0 | 5.0 | | 17 | 28.3 |
| 9 | 60 | 3.0 | 10.0 | | 17 | 28.3 |
| 10 | 60 | 3.0 | | 0.1 | 10 | 16.7 |

TABLE XX

MEDIUM FOR CACAO CELL SUSPENSION (CCS MEDIUM)

| Compounds | Concentration |
|---|---|
| MS Salts | 0.25X |
| Coffee Vitamins | 0.5X |
| Inositol | 100 mg/l |
| Glycine | 25 μM |
| Malt Extract | 100 mg/l |
| Casamino acids | 250 mg/l |
| Coconut Water | 50 mg/l |
| Mannitol | |
| $T_1$ | 44 g/l |
| $T_2$ | 30 g/l |
| $T_3$ | 22 g/l |
| $T_4$ | 0 g/l |
| 2-iP | 3 μM |
| (Autoclave above and filter below) | |
| Sucrose | 30 g/l |
| Kao's Sugars | 1X |
| Kao's Amino Acids | 0.5X |
| Kao's Organic Acids | 1X |
| Kao's Vitamins | 1.0X |
| pH | 5.3 |

10.2 RESULTS

Two culture methods were found to improve the regeneration ability of the cacao suspension cultures: (a) First, the osmoticum effect of the medium containing 22.0 g/l mannitol (autoclaved) and 3 g/l sucrose (filter sterilized) (Table XXI); (b) second, the maintenance of an intermediate size of cell aggregates in the coarse suspension (FIGS. 11B, 11C); the larger aggregates were eliminated during subculture. After the first month of initiation, only selected aggregates were carried in subsequent cultures (FIG. 12A).

Somatic embryo regeneration was accomplished by plating the suspended aggregates on a solid Multi-V medium without 2-iP but supplemented with NAA (4 μM) (Table XXII). The regeneration frequency was determined by counting the number of regenerated embryos per 35 ml of liquid suspension after 4 weeks of plating (FIG. 12B). The screening criterion for embryo regeneration was hypocotyl length equal to or greater than 2 mm, at any developing stage (FIG. 12C).

A successful embryogenic suspension is highly dependent on the quality of the FET inoculated. It is believed that 3 μM 2-iP added in the solid Multi-V medium (Table XVIII) produced the highest amount and best quality of FET in both experiment I (31.1%) and experiment II (61.7%) (Tables XIX and XX). The regeneration characteristics of FET were well maintained in the coarse suspension medium containing 22 g/l mannitol (Table XXI). No vacuolated cells were found during the first 3-months of continued suspension culture. At the same time, the multiplication rate of the FET suspension cultures has been characterized by a doubling in a fresh weight every 15 days.

The regeneration frequency of 13 randomly selected plates is illustrated in Table XXIII. The cell aggregates were plated after 3 months on continuous culture and evaluation was made after 4 weeks on regeneration medium (Table XXII). On average, 15.3 colonies were planted and 137 embryos were regenerated per plate (100×15 mm) or 8.8 cacao somatic embryos were produced per colony. Assuming that one Erlenmeyer flask containing 35 ml of coarse cacao suspension culture will be equivalent to 30 colonies, a total of 274 embryos could be recovered every 15 days. Extrapolating this initial data, using the same culture protocol, it is expected to achieve a yield of 15,658 embryos/liter/month or 282,000 embryos/3 liter bioreactor/6 months. If five units of 3-liter bioreactor vessels are operated simultaneously, approximately 2.8 million embryos/- year can be produced through this protocol for micropropagation purposes.

TABLE XXI
EMBRYO REGENERATION MEDIUM USED FOR CACAO EMBRYOGENIC SUSPENSION CULTURES

| Compounds | Concentration |
|---|---|
| MS Salts | 0.25X |
| Inositol | 100 mg/l |
| Glycine | 50 μM |
| Cysteine | 200 mg/l |
| Malt Extract | 50 mg/l |
| Coconut Water | 50 mg/l |
| PBP-40 | 5 g/l |
| Sucrose | 30 g/l |
| Kao's Vitamins | 1.0X |
| pH | 5.3 |
| NAA | 4.0 μM |
| GELRITE | 2.4 g/l |

TABLE XXII
EVALUATION OF SOMATIC EMBRYO REGENERATION FREQUENCY FROM CACAO EMBRYOGENIC SUSPENSION CULTURES AFTER 4 WEEKS OF CULTURE ON SOLID REGENERATION MEDIUM

| Plate Number | Number of colony/plate | Number of regenerated embryos | Number of embryos per colony |
|---|---|---|---|
| 1 | 15 | 120 | 8.0 |
| 2 | 15 | 140 | 9.1 |
| 3 | 16 | 158 | 9.1 |
| 4 | 16 | 170 | 10.1 |
| 5 | 14 | 118 | 8.4 |
| 6 | 17 | 145 | 8.5 |
| 7 | 15 | 124 | 8.3 |
| 8 | 17 | 140 | 8.2 |
| 9 | 15 | 200 | 13.3 |
| 10 | 15 | 126 | 8.4 |
| 11 | 17 | 124 | 7.3 |
| 12 | 16 | 125 | 7.8 |
| 13 | 12 | 96 | 8.0 |
| Average | 15.3/plate | 137/plate | 8.8/colony |

11. EXAMPLE 6: SOMARIC EMBRYOGENESIS OF CACAO THROUGH CELL SUSPENSION (PROTOCOL II)

11.1 CELL SUSPENSION INITIATION

Primary experiments were conducted to induce embryogenic tissue from explants of the two cacao genotypes (EET-162, UF-667). Approximately 100 explants of each genotype were used per treatment.

Explants were cut into pieces and inoculated onto a solid primary culture medium. The same basic medium composition was used for all experiments (Table XXIII). The effect of hormone concentration and the addition of yeast extract were tested.

The best results were achieved by 2-iP at 10.0 μM, and 6-BA at 5.0 μM (100% embryogenic tissue development). Embryogenic tissue was also achieved with 2-iP at 5.0 and 20.0 μM, and NAA at 5.0 μM. However, the percentage of tissue achieved was lower.

11.2. CELL SUSPENSION DEVELOPMENT EXPERIMENTS

Embryogenic tissue induced using the procedures described in Section 11.1., supra, were suspended in medium. For cell suspension culture the same basic medium (Table XXIII) was used with the addition of hormones. All experiments were initiated with approximately 1 g of embryogenic tissue.

Cell suspensions in medium containing NAA (5 μM) or 2-iP (5–10 μM) have potential for liquid regeneration. The suspensions produced large aggregates and a number of embryos.

TABLE XXIII
BASIC PRIMARY CULTURE MEDIUM

| Compounds | Concentration |
|---|---|
| MS Salts | 0.25X/1.0X |
| Inositol | 100 mg/l |
| Glycine | 50 μM |
| Cysteine | 200 mg/l |
| Malt Extract | 50 mg/l |
| PBP-40 | 5 g/l |
| Sucrose | 30 g/l |
| Gelrite | 2.4 g/l |
| Kao's Vitamins | 1.0X |
| pH | 5.3 |
| Coconut Water | 50 ml/l |
| Hormones | 5 μM NAA or 5–10 μM 2-iP |

The invention described and claimed herein is not to be limited in scope of the specific embodiments herein disclosed, since these embodiments are intended as illustrations of several aspects of the invention. Any equivalent embodiments are intended to be within the scope of this invention. Indeed various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A method for the production of a cacao plantlet capable of developing into a mature cacao plant from a non-zygotic somatic tissue of a mature cacao plant, which method comprises:
   (a) providing a somatic embryo derived from non-zygotic somatic tissue;
   (b) culturing the somatic embryo on a differentiation medium comprising effective amounts of at least growth regulator to obtain a differentiated embryo, wherein said at least one growth regulator is abscisic acid at a concentration of about 0.01 to 300 μM, or a cytokinin at a concentration of about 0.1 to 300 μM, or a gibberellin at a concentration of about 0.05 to 15 μM, or a combination thereof; and
   (c) germinating the differentiated embryo on a germination medium comprising an auxin at a concentration of about 0.05 to 5 μM, a gibberellin at a concentration of about 0.1 to 10 μM, a cytokinin at a concentration of about 0.5 to 30 μM, or a combination thereof to produce a cacao plantlet.

2. The method according to claim 1 in which the at least one growth regulator in the differentiation medium comprises abscisic acid at a concentration of about 0.02 to 150 μM.

3. The method according to claim 1 in which the at least one growth regulator in the differentiation medium comprises a cytokinin at a concentration of about 1 to 300 μM, abscisic acid at a concentration of about 0.02 to 300 μM, and a gibberellin at a concentration of about 0.3 to 15 μM.

4. The method according to claim 1 in which the cytokinin in the differentiation medium is 6-BA.

5. The method according to claim 1 in which the at least one growth regulator in the differentiation medium comprises a cytokinin at a concentration of about 1 to 3 μM, and gibberellic acid at a concentration of about 1 to 15 μM.

6. The method according to claim 1 in which the germination medium is a liquid medium.

7. The method according to claim 1 in which the germination medium comprises an auxin and a gibberellin.

8. The method according to claim 7 in which the auxin is NAA and the gibberellin is gibberellic acid.

9. The method according to claim 1 in which the germination medium comprises an auxin and a cytokinin.

10. The method according to claim 9 in which the auxin is IAA and the cytokinin is 6-BA.

11. The method according to claim 1 in which the germination medium is a solid medium.

12. A method according to claim 1 wherein said at lest one growth regulator in the differentiation medium is abscisic acid at a concentration of about 0.02 to 300 μM 13. A method according to claim 1 wherein said differentiation medium of step (b) further comprises effective amounts of an osmoticum having an osmotic potential in the range of about −5.8 bars to −11 bars.

14. A method according to claim 13 wherein said osmoticum is present in an amount which has an osmotic potential of about −7.0 bars.

15. A method for the production of a cacao plantlet capable of developing into a mature cacao plant from a non-zygotic somatic tissue of mature cacao plant, which method comprises:
  (a) providing a somatic embryo derived from non-zygotic somatic tissue;
  (b) culturing the somatic embryo on a differentiation medium comprising a basal medium under dehydration conditions, which dehydration conditions are achieved by including in the medium a sugar or sugar alcohol osmoticum to provide an osmoticum equivalent in the range of about −5.8 bars to −11 bars, to obtain a differentiated embryo; and
  (c) germinating the differentiated embryo on a germination medium comprising an auxin at a concentration of about 0.05 to 5 μM, a gibberellin at a concentration of about 0.1 to 10 μM, a cytokinin at a concentration of about 0.5 to 30 μM, or a combination thereof, to produce a cacao plantlet.

16. A method for obtaining a somatic embryo from non-zygotic somatic tissue of a mature cacao plant which comprises:
  (a) culturing said cacao non-zygotic somatic tissue on a primary culture medium comprising effective amounts of at least one growth regulator to obtain an immature somatic embryo, wherein said at least one growth regulator in said primary culture medium is a cytokinin at a concentration of about 1 to 15 μM and an auxin at a concentration of about 0.5 to 75 μM; and
  (b) culturing the immature somatic embryo in a regeneration medium which comprises said primary culture medium, to complete the development of the somatic embryo.

17. The method of claim 16 which further comprises, after step (b), the step of:
  (c) culturing tissue of the somatic embryo in an early differentiation medium comprising effective amounts of at least one growth regulator, wherein said at least one growth regulator in said early differentiation medium is an auxin at a concentration of about 0.2 to 10 μM, a cytokinin at a concentration of about 0.2 to 10 μM, abscisic acid at a concentration of about 0.05 to 2.5 μM, a gibberellin at a concentration of about 0.05 to 1 μM, or a combination thereof, to obtain a secondary somatic embryo.

18. A method for producing a cacao plantlet capable of becoming a mature cacao plant from a nonzygotic somatic tissue of a mature cacao plant, which method comprises:
  (a) culturing non-zygotic somatic tissue of a mature cacao plant on a primary culture medium comprising at least one auxin at a concentration of about 2.5 to 50 μM and at least one cytokinin at a concentration of about 0.5 to 5 μM to obtain an immature embryo;
  (b) culturing the immature embryo in an early differentiation medium comprising at least one cytokinin at a concentration of about 0.1 to 10 μM, a gibberellin at a concentration of about 0.05 to 1 μM, and abscisic acid at a concentration of about 0.05 to 2.5 μM, to complete development of a somatic embryo;
  (c) culturing the somatic embryo on a late differentiation medium comprising
    (i) effective amounts of an osmoticum having an osmotic potential in the range of about −5.8 bars to −11 bars, or
    (ii) abscisic acid at a concentration of about 0.02 to 50 μM, or
    (iii) a combination of (i) and (ii), or
    (iv) a combination of (iii) and a natural cytokinin at a concentration of about 0.1 to 10 μM or a synthetic cytokinin at a concentration of about 0.1 to 20 μM, and a gibberellin at a concentration of about 0.1 to 10 μM, or
    (v) a combination of (i) and an auxin at a concentration of about 0.5 to 3 μM, or
    (vi) a combination of (ii) and an auxin at a concentration of about 0.5 to 3 μM, or
    (vii) a combination of (iii) and an auxin at a concentration of about 0.5 to 3 μM, or
    (viii) a combination of (iv) and an auxin at a concentration of about 0.5 to 3 μM to produce a differentiated embryo; and
  (d) germinating the differentiated embryo on a germination medium comprising
    (i) at least one cytokinin at a concentration of about 0.5 to 15 μM, and at least one auxin at a concentration of about 0.1 to 5 μM, or
    (ii) at least one auxin at a concentration of about 0.1 to 5 μM and a gibberellin at a concentration of about 0.1 to 5 μM, or
    (iii) a combination of (i) and a gibberellin at a concentration of about 0.1 to 5 μM, and abscisic acid at a concentration of about 0.01 to 1 μM to produce a cacao plantlet capable of developing into a mature cacao plant.

19. A method for producing a mature cacao plant from a non-zygotic somatic tissue of a mature cacao plant, which method comprises:
  (a) culturing non-zygotic somatic tissue of a mature cacao plant on a primary culture medium comprising at least one synthetic auxin at a concentration of about 2.5 to 50 μM and at least one cytokinin at a concentration of about 0.5 to 5 μM to obtain an immature embryo;

(b) culturing the immature embryo in an early differentiation medium comprising at least one cytokinin at a concentration of about 0.1 to 10 is M, a fibberellin at a concentration of about 0.05 to 1 μM, and abscisic acid at a concentration of about 0.05 to 2.5 μM, to complete development of a somatic embryo;

(c) culturing the somatic embryo on a late differentiation medium comprising
   (i) effective amounts of an osmoticum having an osmotic potential in the range of about −5.8 bars to −11 bars, or
   (ii) abscisic acid at a concentration of about 0.02 to 10 μM, or
   (iii) a combination of (i) and (ii), or
   (iv) a combination of (iii) and a natural cytokinin at a concentration of about 0.1 to 10 μM or a synthetic cytokinin at a concentration of about 0.1 to 20 μM, and a gibberellin at a concentration of about 0.1 to 10 μM, or
   (v) a combination of (i) and an auxin at a concentration of about 0.5 to 3 μM, or
   (vi) a combination of (ii) and an auxin at a concentration of about 0.5 to 3 μM, or
   (vii) a combination of (iii) and an auxin at a concentration of about 0.5 to 3 μM, or
   (viii) a combination of (iv) and an auxin at a concentration of about 0.5 to 3 μM to produce a differentiated embryo; and (d) grafting the differentiated embryo and obtained in step (c) on to cacao seedling root stock to produce a mature cacao plant.

20. The method of claim 18 wherein:
(a) in the primary culture medium, the cytokinin is selected from the group consisting of 2-iP, zeatin and kinetin;
(b) in the early differentiation medium, the cytokinin is zeatin and the gibberelin is gibberellic acid;
(c) in the late differentiation medium, the natural cytokinin is zeatin, the synthetic cytokinin is selected from the group consisting of kinetic, 6-BA and 2-iP, the auxin is selected from the group consisting of NAA and IAA, the gibberellin is gibberellic acid; and
(d) in the germination medium, the gibberellin is gibberellic acid.

21. A method for producing a cacao plantlet capable of developing into a mature cacao plant from a non-zygotic somatic tissue of a mature cacao plant, which method comprises:
(a) culturing non-zygotic somatic tissue of a mature cacao plant on a primary culture medium comprising at least one auxin at a concentration of about 1.5–45 μM to obtain an immature somatic embryo;
(b) culturing the immature somatic embryo in a regeneration medium comprising at least one cytokinin at a concentration of about 0.1 to 10 μM to induce completion of development of a primary somatic embryo;
(c) culturing the primary somatic embryo in said regeneration medium to induce the development of a secondary somatic embryo;
(d) culturing the secondary somatic embryo of step (c) on an early differentiation medium comprising effective amounts of an osmoticum having an osmotic potential in the range of about −5.8 bars to −11 bars, at least one cytokinin at a concentration of about 15 to 100 μM and abscisic acid at a concentration of about 50 to 300 μM to induce differentiation on the secondary somatic embryo;
(e) culturing the somatic embryo obtained in step (d) on a second differentiation medium comprising effective amounts of an osmoticum having an osmotic potential in the range of about −5.8 bars to −11 bars and abscisic acid at a concentration of about 0.02 to 10 μM to obtain a differentiated embryo; and
(f) germinating the differentiated embryo on a germination medium comprising at least one auxin at a concentration of about 0.1 to 5 μM and a gibberellin at a concentration of about 0.1 to 6 μM to produce a cacao plantlet capable of developing into a mature cacao plant.

22. A method of producing a mature cacao plant from a non-zygotic somatic tissue of a mature cacao plant, which method comprises:
(a) producing a cacao plantlet using the method according to claim 21; and
(b) transferring the plantlet to soil to produce a mature cacao plant.

23. The method of claim 21 wherein,
(a) in the regeneration medium, the cytokinin is zeatin;
(b) in the early differentiation medium, the cytokinin is selected from the group consisting of zeatin, kinetin, 6-BA and 2-iP; and
(c) in the germination medium, the gibberellin is gibberellic acid.

24. A method of obtaining a somatic embryo from non-zygotic somatic tissue of a mature cacao plant which comprises:
(a) culturing said cacao non-zygotic somatic tissue on a primary culture medium, which primary culture medium is solidified with a gelling agent and comprises a cytokinin at a concentration of about 0.1 to 30 μM to obtain friable embryogenic tissue;
(b) suspending the friable embryogenic tissue of step (a) in a liquid medium comprising a cytokinin at a concentration of about 0.5 to 15 μM to obtain an immature embryo;
(c) culturing the suspended immature embryo of step (b) in a regeneration medium comprising effective amounts of a osmoticum having an osmotic potential in the range of about −5.8 bars to −11 bars and an auxin at a concentration at about 0.1 to 10 μM to complete the development of a somatic embryo.

25. A method according to claim 24 wherein said primary culture medium further comprises an auxin at a concentration of about 0.5 to 25 μM.

26. A method of obtaining a somatic embryo from non-zygotic somatic tissue of a mature cacao plant which comprises:
(a) culturing said cacao non-zygotic somatic tissue on a primary culture medium, which primary culture medium is solidified with a gelling agent and comprises a cytokinin at a concentration of about 0.5 to 30 μM or an auxin at a concentration of about 0.2 to 20 μM to obtain friable embryogenic tissue;
(b) suspending the friable embryogenic tissue of step (a) in a liquid regeneration medium comprising a cytokinin at a concentration of about 0.5 to 30 μM or an auxin at a concentration of about 0.2 to 20 μM to complete the development of a somatic embryo.

27. A method for the production of a cacao plantlet from a non-zygotic somatic tissue of a parent cacao plant, said plantlet being capable of developing into a mature cacao plant, which method comprises:
(a) providing a somatic embryo derived from non-zygotic somatic tissue;
(b) culturing the somatic embryo on a first differentiation medium comprising
  (i) a cytokinin at a concentration of about 0.1 to 10 μM,
  (ii) a gibberellin at a concentration of about 0.05 to 1 μM,
  (iii) abscisic acid at a concentration of about 0.05 to 2.5 μM, and
  (iv) IAA at a concentration of about 0.1 to 1 μM to obtain a first stage differentiated embryo;
(c) culturing the first stage differentiated embryo in a second differentiation medium comprising abscisic acid at a concentration of about 5–50 μM, to obtain a second stage differentiated embryo; and
(d) germinating the second stage differentiated embryo on a germination medium comprising an auxin at a concentration of about 0.1 to 5 μM, a fibberellin at a concentration of about 0.05 to 6 μM, a cytokinin at a concentration of about 0.5 to 30 μM, or a combination thereof, thereby producing a cacao plantlet.

28. A method for producing a mature cacao plant from a non-zygotic somatic tissue of a mature cacao plant, which method comprises:
(a) obtaining a cacao plantlet using a method according to claim 27,
(b) transferring the cacao plantlet to a hardening box to obtain a hardened cacao plantlet; and
(c) transferring the hardened plantlet to soil to produce a mature cacao plant.

29. A method for the production of cacao plantlet from a non-zygotic somatic tissue of a mature cacao plant, said plantlet being capable of developing into a mature cacao plant, which method comprises:
(a) providing a somatic embryo derived from non-zygotic somatic tissue;
(c) culturing the somatic embryo on series of three differentiation media to obtain a differentiated embryo, wherein:
  (i) the first differentiation medium comprises 6-BA at a concentration of about 2.5 μM, zeatin at a concentration of about 2.5 μM, NAA at a concentration of about 1.5 μM, gibberellic acid at a concentration of about 1.5 μM and abscisic acid at a concentration of about 0.02 μM;
  (ii) the second differentiation medium comprises 6-BA at a concentration of about 5.0 μM, zeatin at a concentration of about 2.0 μM, NAA at a concentration of about 1.5 μM, gibberellic acid at a concentration of about 1.5 μM and abscisic acid at a concentration of about 0.02 μM; and
  (iii) the third differentiation medium comprises 6-BA at a concentration of about 5.0 μM, zeatin at a concentration of about 2.0 μM, NAA at a concentration of about 1.5 μM, gibberellic acid at a concentration of about 1.5 μM, abscisic acid at a concentration of about 0.02 μM, and charcoal at a concentration of about 5 grams/liter,
  each of said three differentiation media further comprising effective amounts of an osmoticum having an osmotic potential in the range of about −5.8 bars to −11 bars; and
(d) germinating the differentiated embryo on a germination medium comprising an auxin at a concentration of about 1 to 1.5 μM, a gibberellin at a concentration of about 1.5 μM, a cytokinin at a concentration of about 2 to 5 μM, or a combination thereof, thereby producing a cacao plantlet.

30. The method of any of claims 1, 15, 16, 17, 18, 19, 21, 22, 23, 24, 26, 27 28 or 29 wherein the non-zygotic somatic tissue is nucellus.

31. The method of any of claims 1, 15, 16, 17, 18, 19, 21, 22, 23, 24, 26, 27, 28 or 29 wherein the non-zygotic somatic tissue is young petals.

32. The method of claim 21, 13, 15, 18, 19, 21, 24 or 29 wherein the osmoticum comprises a sugar or sugar alcohol selected from the group consisting of sucrose, glucose, mannitol, sorbitol and inositol, wherein when said sugar is sucrose, it is present at a concentration of about 80 to 140 grams per liter, and when said sugar or sugar alcohol is glucose, mannitol, sorbitol or inositol, it is present at a concentration of about 45 to 80 grams per liter.

* * * * *